United States Patent
Sugo et al.

(10) Patent No.: US 7,053,053 B2
(45) Date of Patent: May 30, 2006

(54) HUMANIN-LIKE PEPTIDE AND USE THEREOF

(75) Inventors: Tsukasa Sugo, Ibaraki (JP); Masaaki Mori, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 5 days.

(21) Appl. No.: 10/481,044

(22) PCT Filed: Jun. 14, 2002

(86) PCT No.: PCT/JP02/05941

§ 371 (c)(1),
(2), (4) Date: Dec. 15, 2003

(87) PCT Pub. No.: WO02/103018

PCT Pub. Date: Dec. 27, 2002

(65) Prior Publication Data

US 2004/0152101 A1 Aug. 5, 2004

(30) Foreign Application Priority Data

Jun. 15, 2001 (JP) ............................. 2001-182275
Aug. 1, 2001 (JP) ............................. 2001-233532

(51) Int. Cl.
*A61K 38/17* (2006.01)
*C07K 14/47* (2006.01)
*G01N 33/50* (2006.01)
(52) U.S. Cl. ...................................... 514/13; 530/325
(58) Field of Classification Search ................ 436/86; 514/13; 530/325
See application file for complete search history.

(56) References Cited

U.S. PATENT DOCUMENTS 5,346,888 A * 9/1994 Lipsky et al. .................. 514/19

FOREIGN PATENT DOCUMENTS

| EP | 1 221 480 A1 | 7/2002 |
| WO | WO 01/21786 A1 | 3/2001 |
| WO | WO 01/21787 A1 | 3/2001 |
| WO | WO 01/32144 A1 * | 5/2001 |

OTHER PUBLICATIONS

Hashimoto et al., "A rescue factor abolishing neuronal cell death by a wide spectrum of familial Alzheimer's disease genes and Aβ," *PNAS* 98:6336-6341 (2001).

Hillier et al., "Generation and Analysis of 280,000 Human Expressed Sequence Tags," *Genome Research* 6:807-828 (1996).

(Continued)

*Primary Examiner*—Jeffrey Edwin Russel
(74) *Attorney, Agent, or Firm*—David G. Conlin; John B. Alexander; Edwards Angell Palmer & Dodge LLP

(57) ABSTRACT

A novel polypeptide having a cell death inhibitory activity and use thereof is provided. The polypeptide and the polynucleotide encoding it can be used as a diagnostic, therapeutic or prophylactic agent for various diseases and disorders. Certain suitable diseases and disorders which may be diagnosed, treated, or prevented with the polypeptide and the polynucleotide encoding it are selected from neurodegenerative diseases, brain dysfunctions, cancers, immunological disease, infections, gastrointestinal diseases, circulatory diseases, and endocrine diseases. The polypeptide and the polynucleotide encoding it can be used as a cell death inhibitor.

11 Claims, 1 Drawing Sheet

OTHER PUBLICATIONS

Kimberley, "Human DNA sequence from clone RP11-396K16 on chromosome 6 contains ESTs, STSs and GSSs. Contains a mitochondrial 16s rRNA (MTRNR2) pseudogene," Database Accession No. AL356135 XP-002280311. (Last updated Mar. 22, 2001).

Hashimoto et al., "Mechanisms of Neuroprotection by a Novel Rescue Factor Humanin from Swedish Mutant Amyloid Precursor Protein," *Biochemical and Biophysical Research Communications* 283:460-468 (2001).

* cited by examiner ably by using the screening method according to (13)

HUMANIN-LIKE PEPTIDE AND USE THEREOF

TECHNICAL FIELD

The present invention relates to a novel polypeptide regulating biological functions, a DNA encoding the polypeptide and so on. More specifically, the present invention relates to prophylactics and/or therapeutics or diagnostics agents for neurodegenerative diseases, brain dysfunctions, etc.

BACKGROUND ART

Alzheimer's disease is a representative neurodegenerative disease accompanied by progressive dementia and loss of cognitive ability, however effective treatment method for this disease has not been found. Alzheimer's disease is obviously one of the most serious diseases in aging societies at present, and thus development of therapeutics for this disease is extremely significant from the viewpoint of medical economy.

Recently, Hashimoto et al., paid attention to the fact that there are less lesions in the occipital lobe of Alzheimer's disease patients and have cloned a gene by using the "death-trap" method (L. D'Adamio et al., Semin. Immunol., 9:17–23, 1997) from the occipital lobe that inhibits the death of nerve cells into which the causative gene of familial Alzheimer's disease is introduced (Proc. Natl. Acad. Sci. USA 98: 6336–6341, 2001). This gene encodes a peptide designated "humaitin" (WO 01/21787) consisting of 24 residues. A synthetic humanin peptide not only inhibited the death of nerve cells into which the causative gene of familial Alzheimer's disease is introduced, but also the death of nerve cells induced by the addition of β amyloid which is considered to be a potential cause for Alzheimer's disease. These findings suggest that humanin or derivatives thereof might be usable as therapeutic agents for Alzheimer's disease.

Although Alzheimer's disease is a representative neurodegenerative disease accompanied by progressive dementia and loss of cognitive ability, however, effective treatment method has been not found until now.

DISCLOSURE OF THE INVENTION

The present inventors have made intensive and extensive researches directing their attention to these facts. As a result, the present inventors have expected the presence of a humanin-like gene in human genome and found a humanin-like sequence by searching through a human genome database (GEMBLE) using the humanin gene sequence. Further, based on this sequence information, the inventors have succeeded in cloning a gene encoding a humanin-like peptide from a human brain cDNA library. Like humanin, this newly found peptide consisted of 24 residues, of which 6 residues were different from those of humanin. The present inventors have also found that this peptide has an inhibitory effect on the death of nerve cells. As a result of further researches based on these findings, the present invention has been achieved.

The present invention relates to:

(1) A polypeptide comprising an amino acid sequence identical or substantially identical with the amino acid sequence as shown in SEQ ID NO: 4, or an amide, ester or salt thereof;

(2) The polypeptide according to (1) above consisting of the amino acid sequence as shown in SEQ ID NO: 4, or an amide, ester or salt thereof;

(3) A partial peptide of the polypeptide according to (1) above, or amide, ester or salt of the partial peptide;

(4) A polynucleotide comprising a polynucleotide having a nucleotide sequence encoding the polypeptide according to (1) above;

(5) The polynucleotide according to (4) above, wherein the polynucleotide is DNA;

(6) The polynucleotide according to (4) above comprising a nucleotide having the nucleotide sequence as shown in SEQ ID NO: 3;

(7) A polynucleotide comprising a polynucleotide having a nucleotide sequence encoding the partial peptide according to (3) above;

(8) A recombinant vector comprising the polynucleotide according to (4) or (7) above;

(9) A transformant transformed with the recombinant vector according to (8) above;

(10) A method for producing tie polypeptide according to (1) above or an amide, ester or salt thereof or the partial peptide according to (3) above or an amide, ester or salt thereof, comprising culturing the transformant according to (9) above and allowing the polypeptide according to (1) above or the partial peptide according to (3) above to be produced and accumulated;

(11) An antibody to the polypeptide according to (1) above or an amide, ester or salt thereof, or to the partial peptide according to (3) above or an amide, ester or salt thereof;

(12) A polynucleotide having a nucleotide sequence, or a part thereof, complementary to or substantially complementary to the polynucleotide encoding a polypeptide, or a part thereof, comprising an amino acid sequence identical with or substantially identical with the amino acid sequence as shown in SEQ ID NO: 4;

(13) A method for screening for compounds, or salts thereof, that promote or inhibit the activity of the polypeptide according to (1) above or an amide, ester or salt thereof, or the partial peptide according to (3) above or an amide, ester or salt thereof, wherein the method is characterized by using the polypeptide according to (1) above, or an amide, ester or salt thereof, or the partial peptide according to (3) above or an amide, ester or salt thereof;

(14) A kit for screening for compounds, or salts thereof, that promote or inhibit the activity of the polypeptide according to (1) above or an amide, ester or salt thereof, or the partial peptide according to (3) above or an amide, ester or salt thereof, which comprises the polypeptide according to (1) above or an amide, ester or salt thereof, or the partial peptide according to (3) above or an amide, ester or salt thereof;

(15) A compound, or a salt thereof, that promotes the activity of the polypeptide according to (1) above or an amide, ester or salt thereof, or the partial peptide according to (3) above or an amide, ester or salt thereof, which is obtainable by using the screening method according to (13) above or the screening kit according to (14) above;

(16) A compound, or a salt thereof, that inhibits the activity of the polypeptide according to (1) above or an amide, ester or salt thereof, or the partial peptide according to (3) above or an amide, ester or salt thereof, which is obtainable by using the screening method according to (13) above or the screening kit according to (14) above;

(17) A medicine comprising the compound according to (15) or a salt thereof,

(18) A medicine comprising the compound according to (16) or a salt thereof;
(19) A medicine comprising the polypeptide according to (1) above or an amide, ester or salt thereof, or the partial peptide according to (3) above or an amide, ester or salt thereof;
(20) A medicine comprising the polynucleotide according to (4) above;
(21) A diagnostic agent comprising the polynucleotide according to (4) above;
(22) A medicine comprising the antibody according to (11) above;
(23) A diagnostic agent comprising the antibody according to (11) above;
(24) A medicine comprising the polynucleotide according to (12) above;
(25) A diagnostic agent comprising the polynucleotide according to (12) above;
(26) The medicine according to (17), (19) or (20) above, wherein the medicine is a prophylactic and/or therapeutic agent for neurodegenerative disorders or brain dysfunctions;
(27) The medicine according to (26) above, wherein the medicine is a prophylactic and/or therapeutic agent for Alzheimer's disease, Parkinson's disease, Down syndrome, amyotrophic lateral sclerosis, prion disease, Creutzfeldt-Jacob disease, Huntington's chorea, diabetic neuropathy, multiple sclerosis, brain infarction, cerebral hemorrhage, subaraclinoid hemorrhage, ischemic brain diseases, epidural hematoma or subdural hematoma;
(28) The medicine according to (26) above, wherein the medicine is a prophylactic and/or therapeutic agent for Alzheimer's disease;
(29) The medicine according to (17), (19) or (20) above, wherein the medicine is a cell death inhibitor;
(30) The diagnostic agent according to (21), (23) or (25) above, which is a diagnostic agent for diseases accompanied by neurodegeneration;
(31) The diagnostic agent according to (30) above, which is a diagnostic agent for Alzheimer's disease, Parkinson's disease, Down syndrome, amyotrophic lateral sclerosis, prion disease, Creutzfeldt-Jacob disease, Huntington's chorea, diabetic neuropathy, multiple sclerosis, brain infarction, cerebral hemorrhage, subarachnoid hemorrhage, ischemic brain diseases, epidural hematoma or subdural hematoma;
(32) A method of preventing and/or treating neurodegenerative diseases or brain dysfunctions, which is characterized by administering to a mammal an effective amount of the polypeptide according to (1) above or an amide, ester or salt thereof, or the partial peptide according to (3) above or an amide, ester or salt thereof;
(33) A method of preventing and/or treating neurodegenerative diseases or brain dysfunctions, which is characterized by administering to a mammal an effective amount of the polynucleotide according to (4) above;
(34) A method of preventing and/or treating neurodegenerative diseases or brain dysfunctions, which is characterized by administering to a mammal an effective amount of the compound according to (15) above or a salt thereof;
(35) Use of the polypeptide according to (1) above or an amide, ester or salt thereof or the partial peptide according to (3) above or an amide, ester or salt thereof, for producing a prophylactic and/or therapeutic agent for neurodegenerative diseases or brain dysfunctions;
(36) Use of the polynucleotide according to (4) above for producing a prophylactic and/or therapeutic agent for neurodegenerative diseases or brain dysfunctions;
(37) Use of the compound according to (15) above or a salt thereof, for producing a prophylactic and/or therapeutic agent for neurodegenerative diseases or brain dysfunctions.

Further, the polypeptide, the partial peptide, the nucleotide (e.g. DNA) and so forth of the invention may be applicable to molecular markers, tissue markers, chromosome mapping, identification of genetic diseases, diagnosis of disease states, or basic researches such as designing of primers or probes.

BEST MODE FOR CARRYING OUT THE INVENTION

Figure 1:
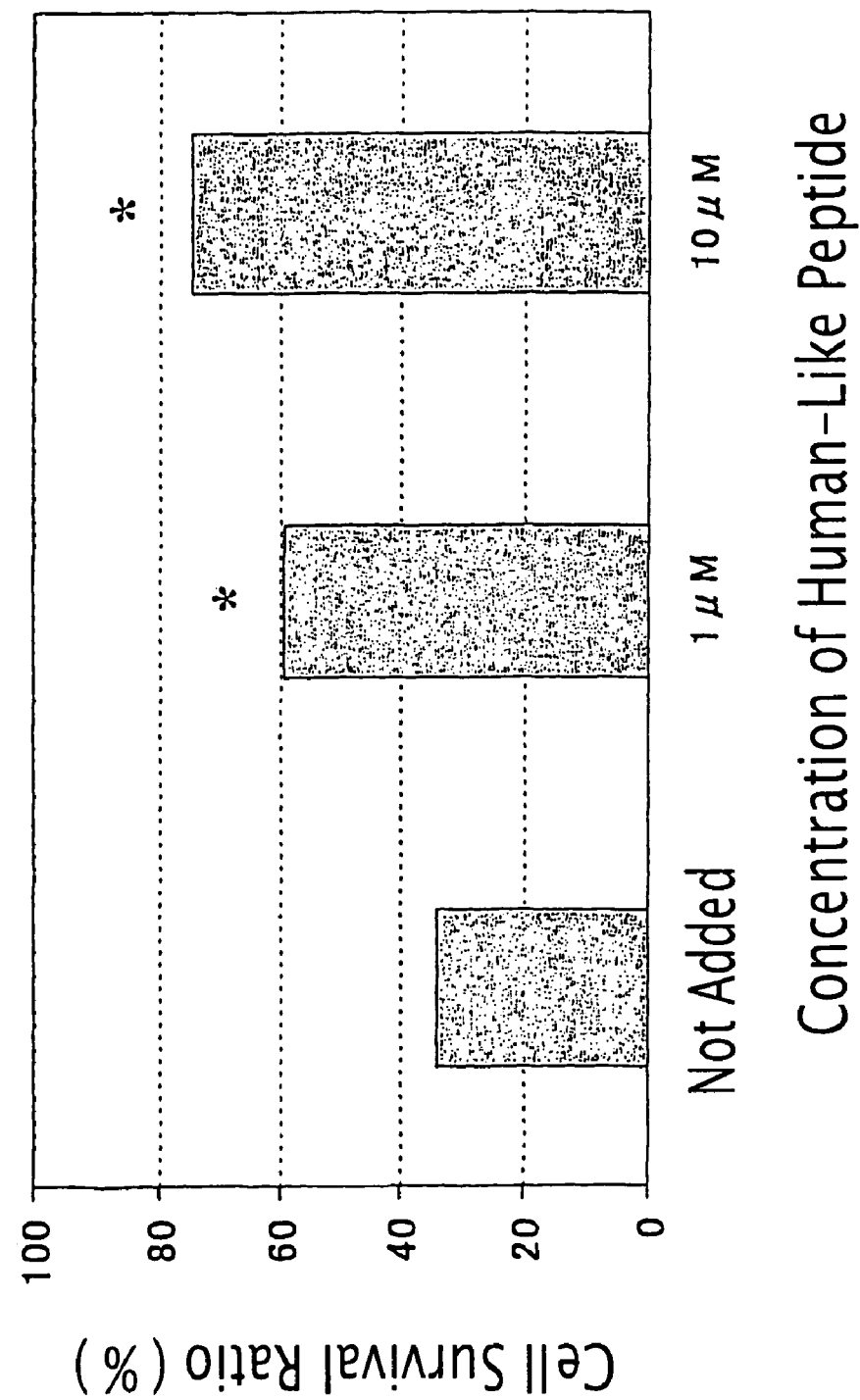
FIG. 1 shows the inhibitory effect of various concentrations of the humanin-like peptide upon glutamic acid-induced cell death of rat adrenal medulla-derived pheochromocytoma cell PC12h. Cell survival ratios are shown taking the survival in the glutamic acid not-added plot as 100%. Mark * represents a significant difference ($p<0.05$) compared to the humanin-like peptide not-added plot.

The polypeptide of the invention comprising an amino acid sequence identical or substantially identical with the amino acid sequence as shown in SEQ ID NO: 4 (hereinafter, sometimes referred to as the "polypeptide of the invention"; sometimes, a polypeptide comprising an amino acid sequence identical or substantially identical with the amino acid sequence as shown in SEQ ID NO: 4 or an amide, ester or salt thereof may also be called the "polypeptide of the invention" collectively) may be a polypeptide derived from cells of any kind (e.g. hepatocytes, splenocytes, nerve cells, glia cells, pancreatic β cells, bone marrow cells, mesangial cells, Langerhan's cells, epidemial cells, epithelial cells, endothelial cells, fibroblasts, fibrous cells, muscle cells, fat cells, immune cells (e.g. macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary cells or interstitial cells, or progenitor cells of these cells, stem cells or cancer cells, etc.) of human or other warm-blooded animals (e.g. guinea pig, rat, mouse, chicken, rabbit, pig, sheep, bovine, monkey, etc.) or any tissue in which such cells are present, such as brain, various parts of brain (e.g. olfactory bulb, amygdaloid nucleus, cerebral basal nucleus, hippocampus, thalamus, hypothalamus, cerebral cortex, medulla oblongata, cerebellum), spinal cord, pituitary gland, stomach, pancreas, kidney, liver, gonad, thyroid, gall-bladder, bone marrow, adrenal gland, skin, muscle, lung, gastrointestinal tracts (e.g. large intestine, small intestine), blood vessels, heart, thymus, spleen, salivary gland, peripheral blood, prostate, testis, ovary, placenta, uterus, bone, cartilage, joint, skeletal muscle, etc. It may also be a recombinant polypeptide or a synthetic polypeptide.

The term "substantially identical" means that the activity of the polypeptide, for example, cell death inhibitory effect (e.g. inhibitory effect against cell death associated with various diseases), cell survival maintaining effect, or prophylactic and/or therapeutic activity (effect) upon neurodegenerative diseases, cancers, immunological diseases, infections, gastrointestinal diseases, circulatory diseases, endocrine diseases, etc. or physiological characteristics of the polypeptide are substantially identical. As long as substitution, deletion, addition or insertion of amino acids does not cause a significant change in physiological properties or chemical properties of a polypeptide, the polypeptide that has undergone the substitution, deletion, addition or insertion may be said substantially identical with the initial polypeptide that has not undergone such substitution, deletion, addition or insertion. The substantially identical substituted amino acid in the above amino acid sequence may be selected from, for example, the other amino acids in the class to which the initial amino acid belongs.

Examples of non-polar (hydrophobic) amino acids include alanine, leucine, isoleucine, valine, proline, phenylalanine, tryptophan and methioine. Examples of polar (neutral) amino acids include glycine, serine, threonine, cysteine, tyrosine, asparagine and glutamine. Examples of positively charged (basic) amino acids include arginine, lysine and histidine. Examples of negatively charged (acidic) amino acids include aspartic acid and glutamic acid.

An amino acid sequence substantially identical wit the amino acid sequence as shown in SEQ ID NO: 4 is not particularly limited as long as the polypeptide comprising the relevant amino acid sequence has an activity (nature) substantially identical with the activity (nature) of a polypeptide comprising the amino acid sequence as shown in SEQ ID NO: 4. For example, an amino acid sequence having about 80% or more, preferably about 85% or more, more preferably about 90% or more, most preferably about 95% or more homology to the amino acid sequence as shown in SEQ ID NO: 4 may be used.

Examples of the activity (nature) of substantially the same quality mentioned above include an activity (effect) that is qualitatively identical to the cell death inhibitory effect (e.g. inhibitory effect against cell death associated with various diseases), cell survival maintaining effect, or prophylactic and/or therapeutic activity (effect) upon neurodegenerative diseases, cancers, immunological diseases, infections, gastrointestinal diseases, circulatory diseases, endocrine diseases, etc. possessed by a polypeptide comprising the amino acid sequence as shown in SEQ ID NO: 4.

More specific examples of polypeptides comprising the amino acid sequence as shown in SEQ ID NO: 4 include the so-called muteins, such as polypeptides comprising (i) the amino acid sequence of SEQ ID NO: 4 wherein one or two or more amino acids (preferably about 1–6, more preferably about 1–3, and still more preferably 1 or 2 amino acids) are deleted therefrom; (ii) the amino acid sequence of SEQ ID NO: 4 wherein one or two or more amino acids (preferably about 1–6, more preferably about 1–3, still more preferably 1 or 2 amino acids) are added thereto; (iii) the amino acid sequence of SEQ ID NO: 4 wherein one or two or more amino acids (preferably about 1–6, more preferably about 1–3, still more preferably 1 or 2 amino acids) are replaced with other amino acids; or (iv) an amino acid sequence which is a combination of these sequences.

When the amino acid sequence is inserted, deleted or substituted as described above, the position of insertion, deletion or substitution is not particularly limited.

As a partial peptide of the polypeptide of the invention (i.e. the partial peptide of the invention), any partial peptide of the above-described polypeptide of the invention may be used. For example, a partial peptide having an activity of substantially the same quality as that of the polypeptide of the invention is preferably used (the term "activity of substantially the same quality" has the same meaning as described above).

However, being different from the polypeptide of the invention, the partial peptide of the invention may be used as antigen for preparing antibodies. Thus, the partial peptide of the invention does not necessarily need to have the activity possessed by the polypeptide of the invention.

More specific examples of the partial peptide of the invention include a partial peptide of the polypeptide of the invention comprising an amino acid sequence identical with or substantially identical with the amino acid sequence as shown in SEQ ID NO: 4.

The term "substantially identical" has the same meaning as defined above in the description of the polypeptide of the invention.

More specific examples of partial peptides comprising an amino acid sequence substantially identical with the amino acid sequence as shown us SEQ ID NO: 4 include the so-called muteins, such as partial peptides comprising (i) the amino acid sequence of SEQ ID NO: 4 wherein one or two or more amino acids (e.g. about 1–20, preferably about 1–15, preferably about 1–10, preferably about 1–5, and more preferably 1 or 2 amino acids) are deleted therefrom; (ii) the amino acid sequence of SEQ ID NO: 4 wherein one or two or more amino acids (e.g. about 1–20, preferably about 1–15, preferably about 1–10, preferably about 1–5, more preferably 1 or 2 amino acids) are added thereto; (iii) the amino acid sequence of SEQ ID NO: 4 wherein one or two or more amino acids (e.g. about 1–5, more preferably 1 or 2 amino acids) are replaced with other amino acids; or (iv) an amino acid sequence which is a combination of these sequences.

When the amino acid sequence is inserted, deleted or substituted as described above, the position of insertion, deletion or substitution is not particularly limited.

Specific examples of the partial peptide of the invention include a peptide having an amino acid sequence spanning from position 19 to position 24 (SEQ ID NO: 7), from position 5 to position 24, from position 1 to position 20, from position 5 to position 20, from position 1 to position 21 or from position 5 to position 21 of the amino acid sequence as shown in SEQ ID NO: 4.

The polypeptide and the partial peptide of the invention also encompass those polypeptides/peptides where substituents on side chains of intramolecular amino acids are protected with appropriate protective groups, or conjugated peptides such as glycopeptides to which sugar chains are attached.

Further, the polypeptide of the invention or the peptide of the invention may exist not only as a monomer but also as a dimer, a trimer, a tetramer, etc. Specifically, possible forms include, but are not limited to, the following: two polypeptides of the invention form a dimer; or two partial peptides of the invention form a dimer; or the polypeptide of the invention and the partial peptide of the invention form a dimer.

Further, the polypeptide and the partial peptide of the invention may comprise any foreign sequence (for example, such as FLAG, His tag, HA tag or HSV tag) that could be an epitope (antibody recognition site) located at, for example, their N-terminal or C-terminal.

The polypeptide and the partial peptide of the invention are expressed in accordance with the conventions for description of peptides, that is, the N-terminus (amino terminus) at the left end and the C-terminus (carboxyl terminus) at the right end. The C-terminus of the polypeptide of the invention (such as a polypeptide comprising the amino acid sequence as shown in SEQ ID NO: 4) may be a carboxyl group (—COOH), a carboxylate (—COO), an amide (—CONH$_2$) or an ester (—COOR).

Examples of R of the above ester group include $C_{1-6}$ alkyl groups (e.g. methyl, ethyl, n-propyl, isopropyl or n-butyl), $C_{3-8}$ cycloalkyl groups (e.g. cyclopentyl or cyclohexyl), $C_{6-12}$ aryl groups (e.g. phenyl or α-naphthyl), $C7_{-14}$ aralkyl groups such as phenyl-$C_{1-2}$ alkyl groups (e.g. benzyl or phenethyl) and α-naphthyl-$C_{1-2}$ alkyl groups (e.g. α-naphthylmethyl). In addition, the ester group also includes pivaloyloxynethyl esters that are universally used as oral esters.

When the polypeptide or the partial peptide of the invention has a carboxyl group (or carboxylate) at any position other than its C-terminus, the carboxyl group may be amidated or esterified; such a polypeptide or partial peptide is also included in the polypeptide or the partial peptide of the invention. The ester in this case may be, for example, any of the esters mentioned above for the C-terminal ester.

Furthermore, the polypeptide or the partial peptide of the invention includes those polypeptides or partial peptides in which the N-terminal amino acid residue (e.g. Met) is protected by a protective group (e.g. $C_{1-6}$ acyl group such as $C_{1-6}$ alkanoyl group (e.g. formyl group or acetyl group)); those polypeptides in which the N-terminal Glu generated through in vivo cleavage is pyroglutaminated; those polypeptides, peptides or partial peptides in which a substituent on a side chain of an amino acid (e.g. —OH, —SH, amino group, imidazole group, indole group, or guannidino group) is protected by an appropriate protective group (e.g. $C_{1-6}$ acyl group such as $C_{1-6}$ alkanoyl group (e.g. formyl group or acetyl group)); and conjugated polypeptides such as the so-called glycopolypeptides to which sugar chains are linked.

As the salt of the polypeptide or the partial peptide of the invention, salts formed with physiologically acceptable acids (e.g. organic or inorganic acids) or bases (e.g. alkali metals) are used. Especially preferable are physiologically acceptable acid addition salts. Examples of such salts include salts formed with inorganic acids. (e.g. hydrochloric acid, phosphoric acid, hydrobromic acid or sulfuric acid) and salts formed with organic acids (e.g. acetic acid, formic acid, propioinc acid, fumaric acid, maleic acid, succinic acid, tartaric acid, citric acid, malic acid, oxalic acid, benzoic acid, methanesulfonic acid or benzenesulfonic acid).

The polypeptide or the partial peptide of the invention can be produced from the afore-mentioned cells or tissues of human or other warm-blooded animals by known purification methods for polypeptides (proteins). Alternatively, the polypeptide or the partial peptide of the invention can be produced by culturing a transformant comprising the polynucleotide (DNA, etc.) of the invention described later encoding the polypeptide or the partial peptide of the invention. It can also be produced in accordance with the procedures for peptide synthesis which are described later.

When the polypeptide or the partial peptide of the invention is produced from tissues or cells of human or non-human mammals, the relevant tissue or cell is homogenized and then the polypeptide of the present invention is extracted with acids, etc. The polypeptide or the partial peptide can be purified and isolated from the resultant extract by a combination of chromatography, such as reversed phase chromatography, ion exchange chromatography and so on.

For the synthesis of the polypeptide or the partial peptide of the invention or a salt or amide thereof, any of the commercial resins available for polypeptide (protein) synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenylhydroxymethyl)phenoxy resin, and 4-(2',4'-dimethoxyphenyl-Fmoc-aminoethyl)phenoxy resin. Using such a resin, amino acids protected at their α-amino groups and side chain functional groups are condensed on the resin according to the amino acid sequence of the polypeptide of interest by conventional condensation methods. At the final stage of the reaction, all protective groups are removed simultaneously with the cleavage of the polypeptide from the resin. Then, in a highly diluted solution, intramolecular disulfide bond formation reaction is carried out to obtain the polypeptide of interest or amide thereof.

With respect to the condensation of the above-described protected amino acids, various activators may be useful for polypeptide synthesis, among all, carbodiimide reagents are especially preferred. Carbodiimide reagents include DCC, N,N'-diisopropylcarbodiimide, and N-ethyl-N'-(3-dimethylaminoprolyl)carbodiimide. For activation by these reagents, protected amino acids may be directly added to the resin with a racemization inhibitor addictive such as HOBt or HOOBt, or protected amino acids may be added to the resin after the protected amino acids may be activated as a corresponding acid anhydride or HOBt ester or HOOBt ester.

The solvent used for the above-mentioned activation of protected amino acids or the condensation thereof with a resin may be appropriately selected from those solvents known to be useful for polypeptide (protein) condensation reactions. Useful solvents include acid amides (e.g. N,N-dimethylformamide, N,N-dimethylacetamide or N-methylpyrrolidone), halogenated hydrocarbons (e.g. methylene chloride, or chloroform), alcohols (e.g. trifluoroethanol), sulfoxides (e.g. dimethyl sulfoxide), ethers (e.g. pylidine, dioxane, tetrahydrofuran), nitrites (e.g. acetonitrile or propionitrile), esters (e.g. methyl acetate or ethyl acetate), and suitable mixtures of these solvents. The reaction temperature may be appropriately selected from the range known to be useful for polypeptide (protein) bond-forming reactions; usually, the temperature is selected from the range from about −20° C. to about 50° C. The activated amino acid derivative is usually used in 1.5- to 4-fold excess. When the condensation is found insufficient as a result of test using the ninhydrin reaction, sufficient condensation can be achieved by repeating reactions without removing protective groups. When sufficient condensation cannot be achieved even by repeating reactions, unreacted amino acids may be acetylated with acetic anhydride or acetylimidazole so that they do not affect subsequent reactions.

Protective groups for the amino group of raw materials include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, and Fmoc.

The carboxyl group can be protected, for example, in the form of an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on); aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected, for example, by esterification or etherification. Examples of suitable groups for this esterification include lower ($C_{1-6}$) alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl.

Protective groups for the phenolic hydroxyl group of tyrosine include Bzl, Cl$_2$-Bzl, 2-nitrobenzyl, BrZ, and t-butyl.

Protective groups for the imidazole ring of listidine include Tos, 4-methoxy-2,3,6-trimethylbenzenesulfonyl, DNP, benzyloxymethyl, Bum, Boc, Trt and Fmoc.

Activated carboxyl groups of raw materials include the corresponding acid anhydrides, azides and active esters (esters of alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide and HOBt). Examples of raw materials with activated amino groups include the corresponding phosphoric acid amides.

Methods for removing (eliminating) protective groups include, for example, catalytic reduction in a hydrogen stream in the presence of a catalyst such as Pd black or Pd-carbon, acid treatment with anhydrous hydrogen fluoride, methanesulfonic acid, trifluoromethanesulfonic acid, trifluoroacetic acid or mixtures thereof, treatment with a base such as diiso-propylethylamine, triethylamine, piperidine, piperazine or the like, and reduction with sodium in liquid ammonia. The elimination reaction by the above-mentioned acid treatment is generally conducted at temperatures of about −20° C. to about 40° C. In the acid treatment, it is effective to add a cation scavenger such as anisole, phenol, thioanisole, m-cresol, p-cresol, dimethylsulfide, 1,4-butanedithiol or 1,2-ethanedithiol. The 2,4-dinitrophenyl group used as the protective group for the imidazole ring of histidine is removed by thiophenol treatment. The formyl group used as the protective group for the indole ring of tryptophan may be removed by the above-mentioned deprotection by the acid treatment in the presence of 12-ethanedithiol, 1,4-butanedithiol or the like, or by alkali treatment using dilute sodium hydroxide, dilute ammonia or the like.

The protection of functional groups which should not be taken part in the reaction and protective groups therefor, the removal of these protective groups and the activation of functional groups involved in the reaction can be appropriately selected from groups or methods known in the art.

An alternative method for obtaining amides of the polypeptide or partial peptide of the invention comprises, for example, protecting the α-carboxyl group of the C-terminal amino acid by amidation, extending the peptide (polypeptide) chain to a desired length on the side of the amino group, preparing a polypeptide with its N-terminal α-amino group selectively deprotected, preparing a polypeptide with its C-terminal carboxyl group selectively deprotected, and condensing these two polypeptides in a mixed solvent such as described above. Details of this condensation reaction are the same as described above. After purification of the protected polypeptide thus obtained by condensation, all the protective groups are removed by the method described above to thereby to provide a crude polypeptide of interest. This crude polypeptide is purified by various known purification techniques and lyophilized to provide the desired polypeptide or partial peptide in an amide form.

A method for obtaining esters of the polypeptide or the partial peptide of the invention, for example, condensing the α-carboxyl group of the C-terminal amino acid with a desired alcohol to prepare the corresponding amino acid ester, and subjecting this ester to the same procedures as described above in the preparation of amides to thereby provide the desired polypeptide or partial peptide in an ester form.

The polypeptide or the partial peptide of the invention can be produced by known methods for peptide synthesis. The method for peptide synthesis may be solid-phase synthesis or liquid-phase synthesis. Briefly, a peptide of interest can be produced by condensing a partial peptide or amino acids capable of constituting the partial peptide of the invention with the residual part thereof and, if the product has protective groups, removing the protective groups. Examples of condensation methods and methods for removal of protective groups known in the art include those described in the following references (i) to (v).

(i) M. Bodanszky & M. A. Ondetti, Peptide Synthesis, Interscience Publishers, New York, 1966
(ii) Schroeder & Luebke, The Peptide, Academic Press, New York, 1965
(iii) Nobuo Izumiya et al., Fundamentals and Experiments in Peptide Synthesis, Maruzen, 1975
(iv) Haruaki Yajima and Shumpei Sakakibara, Biochemical Experiment Series 1, Polypeptide Chemistry IV, 205, 1977, and
(v) Haruaki Yajima (ed.), Development of Drugs (Continued), Vol. 14, Peptide Synthesis, Hirokawa Shoten After the reaction, the polypeptide or the partial peptide of the invention can be isolated and purified by a combination of conventional purification techniques such as solvent extraction, distillation, column chromatography, liquid chromatography, and recrystallization. When the polypeptide thus obtained is a free polypeptide, it can be converted to a suitable salt by know methods or methods based thereon. On the contrary, when the polypeptide is obtained in a salt form, it can be converted to a free polypeptide or another salt by known methods or methods based thereon.

The polynucleotide encoding the polypeptide or the partial peptide of the invention (hereinafter, such polynucleotide is sometimes referred to as the "polynucleotide of the invention" collectively) may be any polynucleotide as long as it comprises a nucleotide sequence encoding the above-described polypeptide or partial peptide of the invention (DNA or RNA; preferably, DNA). The polynucleotide is a DNA or RNA (such as mRNA) encoding the receptor protein of the invention, and may be double-stranded or single-stranded. When the polynucleotide is double-stranded, it may be a double-stranded DNA, a double-stranded RNA, or a DNA:RNA hybrid. When the polynucleotide is single-stranded, it may be a sense strand (i.e. coding strand) or an anti-sense strand (i.e. non-coding strand).

The DNA encoding the polypeptide or the partial peptide of the invention may be genomic DNA, cDNA derived from the above-mentioned cells or tissues, or synthetic DNA. Vectors used for library construction may be any vectors such as bacteriophage, plasmid, cosmid, phagemid, and so on. Alternatively, total RNA or mRNA fraction may be prepared from the above-mentioned cells or tissues, followed by direct amplification by reverse transcriptase polymerase chain reaction (hereinafter, abbreviated to as "RT-PCR").

With respect to the DNA encoding the polypeptide of the invention, the DNA may be any DNA as long as it comprises a DNA encoding a polypeptide having an activity (nature) of substantially the same quality as that of the polypeptide of the invention [e.g. cell death inhibitory effect (inhibitory effect upon cell death associated with diseases), cell survival maintaining effect, prophylactic and/or therapeutic activity (effect) on neurodegenerative diseases, cancers, immunological diseases, infections, gastrointestinal diseases, circulatory diseases and endocrine diseases] and yet encodes a polypeptide having a nature of substantially the same quality as that of the polypeptide of the invention. Specific examples of the polynucleotide encoding the polypeptide of the invention include, but are not limited to, DNAs comprising a DNA having the nucleotide sequence as shown in SEQ ID NO: 3.

DNAs which are capable of hybridizing to the nucleotide sequence as shown in SEQ ID NO: 3 under high stringency conditions may also be enumerated as the DNA encoding the polypeptide of the invention. For example, DNAs comprising a nucleotide sequence having about 80% or more, preferably about 85% or more, still more preferably about 90% or more homology to the nucleotide sequence as shown in SEQ ID NO: 3 may be used.

Hybridization can be carried out according to known methods or methods based thereon, e.g. those methods described in "Molecular Cloning," 2nd Ed. (J. Sambrook et al., Cold Spring Harbor Lab. Press, 1989). When commercial libraries are used, hybridization can be carried out in accordance with the methods described in the attached instructions; more preferably, hybridization is carried out under high stringency conditions.

"High stringency conditions" refers to, for example, conditions where sodium concentration is about 19–40 mM, preferably about 19–20 mM, and temperature is about 50–70° C., preferably about 60–65° C.

As a DNA encoding a polypeptide having the amino acid sequence as shown in SEQ ID NO: 4, a DNA having the nucleotide sequence as shown in SEQ ID NO: 3 may be used, for example. As a DNA encoding the partial peptide of the invention, any DNA encoding the partial peptide of the invention may be used. Specific examples of such DNA include a DNA comprising the nucleotide sequence as shown in SEQ ID NO: 4.

The cloning method of a DNA encoding the full length of the polypeptide or the partial peptide of the invention can be performed either by PCR amplification from genomic DNA or cDNA using synthetic DNA primers each having a partial nucleotide sequence of the polypeptide or partial peptide of the invention, or by a method where a DNA fragment is selected by hybridizing DNA inserted into an appropriate vector (i.e. library) to a DNA probe labeled with a ratio isotope or enzyme, the DNA probe being a DNA fragment or a synthetic DNA encoding a part or full length of the polypeptide or partial peptide of the invention. The hybridization can be carried out, for example, according to the method described in "Molecular Cloning", 2nd Edition (J. Sambrook et al., Cold Spring Harbor Lab. Press, 1989). When commercial libraries are used, the hybridization can be carried out according to the attached instructions.

Substitution of the nucleotide sequence of a DNA can be performed by known methods such as ODA-LA PCR, the gapped duplex method, the Kunkel method and the like using PCR, known kits such as Mutan™-Super Express Km (Takara), Mutan™-K (Takara), etc.

The DNA encoding the cloned polypeptide of the invention may be used as it is or after digestion with restriction enzymes or addition of linkers, depending on purposes. The DNA may have ATG at its 5' end as a translation initiation codon and TAA, TGA, or TAG at its 3' end as a translation termination codon. The translation initiation and termination codons may also be added by using appropriate synthetic DNA adapters.

Expression vectors for the polypeptide or the partial peptide of the invention can be prepared by, for example, (a) cutting out desired DNA fragment from a DNA encoding the polypeptide or the partial peptide of the invention and (b) ligating the DNA fragment to an appropriate expression vector downstream of its promoter.

Examples of vectors useful in the invention include plasmids derived from *Escherichia coli* (e.g. pBR322, pBR325, pUC12, and pUC13); plasmids derived from *Bacillus subtilis* (e.g. pUB110, pTP5 and pC194); plasmids derived from yeast (e.g. pSH19 and pSH15); bacteriophages such as λ-phage; animal viruses such as retrovirus, vaccinia virus, baculovirus; and other vectors such as pA1-11, pXT1, pRc/CMV, pRc/RSV, pcDNAI/Neo and so on.

Any promoter may be used in the invention as long as it is appropriate for the host that will be used for expressing a gene of interest. When the host is an animal cell, examples of promoters useful in the invention include SRα promoter, SV40 promoter, LTR promoter, CMV promoter, HSV-TK promoter and β-actin promoter.

Among these promoters, CMV (cytomegalovirus) promoter, SRα promoter or the like is preferably used. When the host is an *Escherichia* bacterium, trp promoter, lac promoter, recA promoter, λ$P_L$ promoter, lpp promoter, T7 promoter or the like is preferably used. When the host is a *Bacillus* bacterium, SPO1 promoter, SPO2 promoter, penP promoter or the like is preferably used. When the host is a yeast, PHO5 promoter, PGK promoter, GAP promoter, ADH promoter, or the like is preferably used. When the host is an insect cell, polyhedrin promoter, P10 promoter or the like is preferably used.

The expression vectors may, if desired, further comprise enhancers, splicing signals, polyadenylation signals, selective markers, SV40 replication origin (hereinafter, sometimes abbreviated to "SV40 ori") and the like. Examples of selective markers useful in the invention include dihydrofolate reductase (hereinafter, sometimes abbreviated to "dhfr") gene [methotorexate (MTX) resistance], ampicillin resistance gene (hereinafter, sometimes abbreviated to "Amp"), neomycin resistance gene [hereinafter, sometimes abbreviated to "Neo"': Geneticin resistance] and the like. When dhfr gene-deficient Chinese hamster cells are used in combination with dhfr gene as a selective marker, recombinant cells may be selected even in a thymidine-free medium.

Furthermore, a signal sequence appropriate for the host may be added, if necessary, to the N-terminal of the polypeptide of the invention. When the host is an *Escherichia* bacterium, the utilizable signal sequences may include PhoA signal sequence, OmpA signal sequence or the like may be added. When the host is a *Bacillus* bacterium, α-amylase signal sequence, subtilisin signal sequence, or the like may be added. When the host is yeast, MFα signal sequence, SUC2 signal sequence or the like may be added. When the host is an animal cell, insulin signal sequence, α-interferon signal sequence, antibody molecule signal sequence, or the like may be used.

Using the thus constructed vector comprising a DNA encoding the polypeptide or the partial peptide of the invention, transformants can be prepared.

Examples of hosts useful for this purpose include bacteria belonging to the genus *Escherichia*, bacteria belonging to the genus *Bacillus*, yeasts, insect cells, insects, and animal cells.

Specific examples of bacteria belonging to the genus *Escherichia* useful in the invention include *E. coli* K12 DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)]), HB101

[Journal of Molecular Biology, Vol, 41, 459 (1969)] and C600 [Genetics, Vol. 39, 440 (1954)].

Specific examples of bacteria belonging to the genus *Bacillus* useful in the invention include *B. subtilis* MI114 [Gene, Vol. 24, 255 (1983)] and 207–21 [Journal of Biochemistry, Vol. 95, 87 (1984)].

Specific examples of yeasts useful in the invention include *Saccharomyces cerevisiae* AH22, AH22R⁻, NA87-11A, DKD-5D and 20B-12, *Schizosaccharomyces pombe* NCYC1913 and NCYC2036, and *Pichia pastoris* KM71.

Specific examples of insect cells useful in the invention include, when the virus used is AcNPV, a cell line derived from larvae of *Spodoptera frugiperda* (Sf cells), MG1 cells derived from the midgut of *Trichoplusia ni*, High Five™ cells derived from eggs of *Trichoplusia ni*, *Mamestra brassicae*-derived cells and *Estigmena acrea*-derived cells. When the virus used is BmNPV, insect cells such as a silkworm-derived cell line (*Bombyx mori* N cells; BmN cells) may be used. Specific examples of Sf cells useful in the invention include Sf9 cells (ATCC CRL 1711) and Sf21 cells [both disclosed in Vaughn J. L. et al., In Vivo, 13, 213–217 (1977)].

Specific examples of insects useful in the invention include larvae of silkworm (Maeda et al., Nature, 315, 592 (1985)).

Specific examples of al cells useful in the invention include simian cell COS-7, Vero cells, Chinese hamster cell CHO (hereinafter, abbreviated to "CHO cells"), sdhfr gene-deficient Chinese hamster cell CHO (hereinafter, abbreviated to "CHO(dhfr⁻) cells"), mouse L cells, mouse AtT-20 cells, mouse myeloma cells, rat GH3 cells, and human FL cells.

Transformation of bacteria belonging to the genus *Escherichia* can be performed in accordance with methods disclosed, for example, in Proc. Natl. Acad. Sci. USA, Vol. 69, 2110 (1972) and Gene, Vol. 17, 107(1982).

Transformation of bacteria belonging to the genus *Bacillus* can be performed in accordance with methods disclosed, for example, in Molecular & General Genetics, Vol. 168, 111 (1979).

Transformation of yeasts can be performed in accordance with methods disclosed, for example, in Methods in Enzymology, 194, 182–187(1991) and Proc. Natl. Acad. Sci. USA, Vo. 75, 1929 (1978).

Transformation of insect cells or insects can be performed in accordance with methods disclosed, for example, in Bio/Technology, 6, 47–55 (1988).

Transformation of animal cells can be performed by methods disclosed, for example, in Cell Engineering, Separate Vol. 8, New Cell Engineering Experiment Protocol, 263–267 (1995) (Shujunsha Co.) and Virology, Vol. 52, 456 (1973).

Thus, transformants transformed with the expression vector comprising a DNA encoding the polypeptide can be obtained.

As a medium to culture transformants obtained from *Escherichia* or *Bacillus* bacteria as hosts, a liquid medium is appropriate. The medium may contain carbon sources, nitrogen sources, minerals, and so on which are necessary for the growth of the transformant. As carbon sources, glucose, dextrin, soluble starch, sucrose or the like may be enumerated. As nitrogen sources, organic or inorganic substances such as ammonium salts, nitrates, corn steep liquor, peptone, casein, meat extract, bean cake, potato extract, or the like may be enumerated. As minerals, calcium chloride, sodium dihydrogen phosphate, magnesium chloride, or the like may be enumerated. Further, yeast, vitamins, growth-promoting factors, etc. may also be added to the medium. Preferable pH of the medium is about 5–8.

As a medium to culture *Escherichia* bacteria, M9 medium containing glucose and casamino acid [Miller, Journal of Experiments in Molecular Genetics, 431–433, Cold Spring Harbor Laboratory, New York, (1972)] is preferable, for example. If necessary, drugs such as 3 β-indolyl acrylic acid can be added to the medium to improve the efficiency of the promoter.

When the host is an *Escherichia* bacterium, the transformant is cultured usually at about 15–43° C. for about 3–24 hours. If necessary, aeration and stirring may be applied.

When the host is a *Bacillus* bacterium, the transformant is cultured usually at about 30–40° C. for about 6–24 hours. If necessary, aeration and stirring may also be applied.

As a medium to culture transformants obtained from yeasts as hosts, a medium such as Burkholder minimum medium [Bostian, K. L. et al., Proc. Natl. Acad. Sci. USA. Vol. 77, 4505 (1980)] or SD medium containing 0.5% casamino acid [Bitter, G. A. et al., Proc. Natl. Acad. Sci. USA, Vol. 81, 5330 (1984)] may be used, for example. It is preferable that the pH of the medium be adjusted to about 5–8. The transformant is cultured usually at about 20–35° C. for about 24–72 hours. If necessary, aeration and stirring may be applied.

As a medium to culture transformants obtained from insect cells or insects as hosts, Grace's Insect Medium [Grace, T.C.C., Nature, 195, 788 (1962)] supplemented with additives such as inactivated 10% bovine serum may be used, for example. It is preferable that the pH of the medium be adjusted to about 6.2–6.4. The transformant is cultured usually at about 27° C. for about 3–5 days. If necessary, aeration and stirring may be applied.

As a medium to culture transformants obtained from animal cells as hosts, examples of useful media include MEM medium [Science, Vol. 122, 501 (1952)], DMEM medium [Virology, Vol. 8, 396 (1959)], RPMI 1640 medium [Journal of the American Medical Association, Vol. 199, 519 (1967)] and 199 medium [Proceedings of the Society of the Biological Medicine, Vol. 73, 1 (1950)] each containing about 5–20% fetal calf serum. Preferable pH of the medium is from about 6 to about 8. The transformant is cultured usually at about 30–40° C. for about 15–60 hours. If necessary, aeration and stirring may be applied.

Thus, it is possible to allow the transformant to produce the polypeptide or the partial peptide of the invention within cells or cell membranes, or preferably, out of cells.

Separation and purification of the polypeptide or the partial peptide of the invention from the resultant culture can be carried out, for example, according to the methods described below.

For extraction of the polypeptide or the partial peptide of the invention from cultured microorganisms or cells, the microorganism cells are harvested by known methods after the cultivation, suspended in a suitable buffer, and disrupted by sonication or by lysozyme and/or freezing and thawing, etc. Then, a crude extract of the polypeptide extract is obtained by centrifugation or filtration. The buffer may contain a protein denaturing agent such as urea or guanidine hydrochloride, or a surfactant such as Triton X-100™. If the polypeptide is secreted into the culture broth, the supernatant is separated from the microorganisms or cells after completion of the cultivation and collected by known methods.

Purification of the polypeptide or the partial peptide of the invention contained in the resultant culture supernatant or extract can be performed by an appropriate combination of known methods for separation and purification. These known methods include methods utilizing solubility (such as salting out or sedimentation with solvents), methods mainly utilizing difference in molecular weight (such as dialysis, ultrafiltration, gel filtration and SDS-polyacrylamide gel electrophoresis), methods utilizing difference in electric charge (such as ion-exchange chromatography), methods utilizing specific affinity (such as affinity chromatography), methods utilizing difference in the hydrophobicity (such as reversed-phase high-performance liquid chromatography), and methods utilizing difference in isoelectric point (such as isoelectric electrophoresis).

When the thus obtained polypeptide or partial peptide of the invention is a free form, it can be converted into the above-described salt by known methods or methods based thereon. On the contrary, when the protein of interest is obtained in a salt form, the salt can be converted into a free form or another salt according to known methods or methods based thereon.

The polypeptide or the partial peptide produced by the transformant can be arbitrarily modified or a part thereof can be removed therefrom by using an appropriate protein modification enzyme before or after the purification. Examples of such enzymes include trypsin, chymotrypsin, arginyl endopeptidase, protein kiiase and glycosidase.

The presence of the thus produced polypeptide or partial peptide of the invention can be measured by enzyme immunoassays, Western blot analysis, etc. using specific antibodies.

Alternatively, the presence of the polypeptide or the partial peptide of the invention can be measured by fusing any foreign peptide sequence (e.g. FLAG, HIS tag, myc tag, HA tag, or HSV tag) that can be an epitope (antibody recognition site) to the N-terminal, C-terminal or some other site of the polypeptide as described earlier and then detecting chemiluminescence or the like using an antibody that recognizes the above peptide sequence.

Antibodies to the polypeptide or the partial peptide of the invention (hereinafter, sometimes referred to as the "antibody of the invention") may be either polyclonal antibodies (hereinafter, sometimes referred to as the "polyclonal antibody of the invention") or monoclonal antibodies (hereinafter, sometimes referred to as the "monoclonal antibody of the invention") as long as they can recognize the polypeptide or the partial peptide of the invention.

The antibody to the polypeptide or the partial peptide of the invention can be prepared using the polypeptide or the partial peptide of the invention as antigen and according to known methods for antibody or anti-serum preparation.

[Preparation of Monoclonal Antibodies]

(a) Preparation of Monoclonal Antibody-Producing Cells

The polypeptide or the partial peptide of die invention is administered to warm-blooded animals either alone or together with a carrier or diluent to a site capable of producing antibodies upon the administration. In order to enhance the ability to produce antibodies, complete Freund's adjuvants or incomplete Freund's adjuvants may also be administered. The administration is usually carried out once in every two to six weeks and two to ten times in the total. Examples of warm-blooded animals useful in the invention include monkey, rabbit, dog, guinea pig, mouse, rat, sheep, goat and chicken. Among them, mouse or rat is used preferably.

In the preparation of monoclonal antibody-producing cells, individuals with detectable antibody titers are selected from warm-blooded animals (e.g. mice) immunized with antigen. Then, the spleen or lymph nodes are collected from them two to five days after the final immunization, and antibody-producing cells contained therein are fused with myeloma cells of a homologous or heterologous animal to thereby obtain monoclonal antibody-producing hybridomas. Measurement of antibody titers in antisera may be carried out, for example, by reacting a labeled polypeptide (which will be described later) with the antiserum, followed by measuring the activity of the labeling agent bound to the antibody. The cell fusion may be carried out by a known method, for example, the method of Koehler and Milstein (Nature, 256, 495, (1975)). Examples of useful fusion promoters include polyethylene glycol (PEG), Sendai virus, etc. Preferably, PEG is used.

Examples of myeloma cells useful in the invention include myeloma cells of warm-blooded animals such as NS-1, P3U1, SP2/0, AP-1, etc. Preferably, P3U1 is used. A preferable ratio of the number of antibody-producing cells used (spleen cells) to the number of myeloma cells is from about 1:1 to about 20:1. When PEG (preferably, PEG 1000 to PEG 6000) is added at a concentration of about 10–80% and the resultant cell mixture is incubated at 20–40° C. (preferably, at 30–37° C.) for about 1–10 minutes, an efficient cell fusion can be achieved.

Various methods may be used for screening for monoclonal antibody-producing hybridomas. For example, hybridoma culture supernatant is added to a solid phase (e.g. microplate) on which the polypeptide antigen has been adsorbed either directly or with a carrier. Then, a radioactively or enzymatically labeled anti-immunoglobulin antibody (anti-mouse immunoglobulin antibody is used when mouse cells are used in the cell fusion) or protein A is added thereto to detect monoclonal antibodies bound to the solid phase. Alternatively, a method may be used in which hybridoma culture supernatant is added to a solid phase on which an anti-immunoglobulin antibody or protein A has been adsorbed; then, a radioactively or enzymatically labeled polypeptide is added thereto to thereby detect monoclonal antibodies bound to the solid phase.

Selection of monoclonal antibodies may be carried out by known methods or methods based on them. Usually, selection can be carried out in a medium for culturing animal cells supplemented with HAT (hypoxanthine, aminopterin and thymidine). As a medium for selection and culturing, any medium may be used as long as hybridomas are capable of growing therein. Examples of useful media include RPMI 1640 medium containing about 1–20% (preferably about 10–20%) of fetal calf serum, GIT medium (Wako Pure Chemical Industries, Ltd.) containing about 1–20% of fetal calf serum and a serum-free medium for hybridoma cultivation (SFM-101; Nissui Pharmaceutical Co.). The cultivation temperature is usually about 20–40° C., preferably about 37° C. The cultivation period is usually from five days to three weeks, preferably one to two weeks. The cultivation may be carried out usually under 5% carbon dioxide. The antibody titer of hybridoma culture supernatant may be measured in the same manner as in the above-mentioned measurement of the antibody titers in antisera.

(b) Purification of the Monoclonal Antibodies

Separation and purification of monoclonal antibodies may be carried out by conventional methods, such as methods for separating/purifying immunoglobulin [e.g. salting-out, alcohol precipitation, isoelectric precipitation, electrophoresis, adsorption/desorption using ion exchangers (e.g. DEAE), ultracentrifugation, gel filtration, specific purification methods in which only an antibody is collected by means of an antigen-binding solid phase or active adsorbent such as protein A or protein G, followed by dissociation of the bond].

[Preparation of Polyclonal Antibodies]

The polyclonal antibody of the invention can be produced by known methods or methods based on them. For example, an immunogen (antigen polypeptide) per se or a complex of the immunogen and a carrier protein is prepared. Then, using the immunogen or the complex, warm-blooded animals are immunized in the same manner as described for the production of monoclonal antibodies. Fractions containing the antibody against the polypeptide or the partial peptide of the invention are harvested from the immunized animals, followed by separation and purification of the antibody.

With respect to the immunogen-carrier protein conjugate for use in the immunization of warm-blooded animals, the kind of carrier protein and the mixing ratio of the carrier and the hapten are not particularly restricted as long as antibodies are produced efficiently against the hapten cross-linked to the carrier. For example, bovine serum albumin, bovine thyroglobulin, hemocyanin, or the like is coupled to the hapten at a weight ratio of about 0.1–20:1, preferably about 1–5:1.

A variety of condensing agents can be used for the coupling between the hapten and the carrier. For example, glutaraldehyde, carbodiimide, maleimide, or active ester reagents containing a thiol or dithiopyridyl group may be used.

The condensation product is administered to a warm-blooded animal either alone or together with a carrier or diluent at a site capable of producing antibodies upon the administration. In order to enhance the antibody production ability, complete Freund's adjuvant or incomplete Freund's adjuvant may also be administered. Administration is carried out generally once in about every 2–6 weeks and about 3–10 times in the total.

Polyclonal antibodies can be recovered from the blood, abdominal dropsy or other body fluid, preferably from the blood, of the warm-blooded animal immunized as described above.

Polyclonal antibody titers in antisera can be determined in the same manner as described above for the determination of monoclonal antibody titers in antisera. The separation and purification of polyclonal antibodies can be carried by the same methods for separation and purification of immunoglobulin as those described for the separation and purification of monoclonal antibodies.

With respect to the antisense polynucleotide having a nucleotide sequence complementary to or substantially complementary to the polynucleotide of the invention, any antisense polynucleotide may be used as long as it has a nucleotide sequence complementary to or substantially complementary to the polynucleotide of the invention and has an effect capable of inhibiting the expression of the polynucleotide (DNA).

A nucleotide sequence substantially complementary to the polynucleotide of the invention refers to, for example, a nucleotide sequence having about 70% or more, preferably about 80% or more, more preferably about 90% or more, most preferably about 95% or more homology to the full-length or a partial nucleotide sequence of the complementary nucleotide sequence to the polynucleotide of the invention (i.e., the complementary strand to the DNA of the invention). Particularly preferable is an antisense polynucleotide having about 70% or more, preferably about 80% or more, more preferably about 90% or more, most preferably about 95% or more homology to a part of the complementary strand to the polynucleotide of the invention encoding an N-terminal portion of the polypeptide of the invention (e.g. nucleotide sequence encoding a region neighboring the initiation codon). These antisense polynucleotides can be synthesized with known DNA synthesizers.

When the polypeptide of the invention has a signal peptide, the peptide is efficiently secreted out of cells and manifests as a humoral factor important biological activities for signal transduction, self-defense, etc.

Hereinbelow, uses of the polypeptide of the invention, the partial peptide of the invention (sometimes, these two and salts thereof are collectively referred to as the "polypeptide of the invention"), the polynucleotide encoding the polypeptide of the invention (the polynucleotide of the invention), the antibody to the polypeptide of the invention (the antibody of the invention) and the antisense polynucleotide of the invention will be described.

(1) Therapeutic and/or Prophylactic Agents for Various Diseases where the Polypeptide of The Invention is Involved The polypeptide of the invention exists in vivo, and has cell death inhibitory effect, cell survival maintaining effect, etc. When the polypeptide or the polynucleotide (e.g. DNA) of the invention is mutative, deficient, or expressed at an mutatively decreased or enhanced level, various diseases including diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfuncytions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases develop.

Therefore, the polypeptide or the polynucleotide of the invention can be used as a medicine of low toxicity and high safety, for example, as a cell death inhibitor and as a prophylactic and/or therapeutic agent for various diseases including diseases accompanied by neurodegeneration, such as neurodegenerative diseases [e.g. Alzheimer's disease (familial Alzheimer's disease, juvenile Alzheimer's disease, sporadic Alzheimer's, disease, etc.), Parkinson's disease, Down syndrome, amyotropluc lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases. Still preferably, the polypeptide or the polynucleotide of the invention can be used as a prophylactic and/or therapeutic agent for Alzheimer's disease.

For example, when a patient is suffering from insufficient or mutative signal transduction resulted from decrease or deficiency of the polypeptide of the invention in his/her body, it is possible to restore sufficient or normal function of the polypeptide of the invention by (1) administering the polynucleotide of the invention to the patient and thereby allowing the polypeptide of the invention to be expressed in the body; (2) introducing the polynucleotide of the invention into cells to thereby allow the expression of the polypeptide of the invention, and then transplanting the cells into the patient; or (3) administering the polypeptide of the invention to the patient.

When the polynucleotide of the invention is used as the above-mentioned medicine, the polynucleotide (e.g. DNA) per se or the polynucleotide inserted into an appropriate vector such as a retrovirus vector, adenovirus vector, adeno-associated virus vector, etc. may be administered to human or other warm-blooded animals using conventional means. The polynucleotide of the invention may be administered as it is or after formulation with physiologically acceptable carriers such as adjuvants to promote its uptake, by means of a gene gun or a catheter such as hydrogel catheter.

When the polypeptide of the invention is used as the above-described prophylactic and/or therapeutic agent, at least 90%, preferably 95% or more, more preferably 98% or more, still preferably 99% or more purified polypeptide of the invention is used.

The polypeptide of the invention may be used, for example, orally in the form of tablets (sugar-coated, if necessary), capsules, elixirs, microcapsules or the like; or parenterally in the form of injections such as aseptic solutions or suspensions in water or other pharmaceutically acceptable liquids. These preparations may be produced, for example, by mixing the polypeptide of the invention with physiologically acceptable carriers, flavoring agents, excipients, vehicles, antiseptics, stabilizers, binders, etc. in unit dosage forms required for preparing generally approved pharmaceutical preparations. The amounts of active ingredients in these formulations are decided so that an appropriate dose within the specified range can be obtained.

Examples of additives which may be mixed in tablets, capsules, etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is capsule, liquid carrier such as oils and fats may further be included in addition to the above-mentioned materials. Sterile compositions for injection can be formulated according to conventional practices in pharmaceutical manufacturing, e.g., by dissolving or suspending active ingredients, naturally occurring vegetable oils such as sesame oil, coconut oil, etc. in vehicles such as water for injection.

Examples of aqueous liquids for injection include physiological saline and isotonic solutions containing glucose and other auxiliary agents (e.g. D-sorbitol, D-mannitol, sodium chloride, etc.). They may be used in combination with a suitable auxiliary solubilizer such as alcohol (e.g. ethanol, etc.), polyalcohol (e.g. propylene glycol, polyethylene glycol, etc.), nonionic surfactant (e.g. Polysorbate 80™, HCO-50, etc.). Examples of oily liquids for injection include sesame oil, soybean oil, etc. They may be used in combination with an auxiliary solubilizer such as benzyl benzoate, benzyl alcohol, etc. In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), preservatives (e.g. benzyl alcohol, phenol, etc.), antioxidants, etc. may also be admixed therewith. Usually, the prepared injections are filled in appropriate ampoules.

Vectors into which the polynucleotide of the invention has been introduced may also be formulated as described above and usually used parenterally.

Thus obtained preparations are safe and of low toxicity and they can be administered to mammals (e.g., human, rat, mouse, guinea pig, rabbit, sheep, pig, bovine, horse, cat, dog, monkey, etc.).

Dose levels of the polypeptide of the invention may vary depending upon the target disease, the patient to be treated, administration route, and so on. When the polypeptide of the invention is administered orally for treating Alzheimer's disease, generally the polypeptide of the invention is administered to adult patients (60 kg in body weight) at a dose of about 1–1000 mg/day, preferably about 10–500 mg/day, more preferably about 10–200 mg/day. With respect to parenteral administration, for example, when the polypeptide of the invention is administered to adult patients (60 kg in body weight) in the form of an injection for treating a neurodegenerative disease such as Alzheimer's disease, it is convenient to inject the polypeptide of the invention into the affected part of the body at a dose of about 1–1000 mg/day, preferably about 1–200 mg/day, and more preferably about 10–100 mg/day, though the dose per administration may vary depending on the patient to be treated, the target disease, etc. For other animals, corresponding doses may be administered after conversion of the above-mentioned values per 60 kg based on actual body weights.

(2) Screening for Candidate Compounds for Medicine to Treat Diseases

Since the polypeptide of the invention exists in vivo, a compounds, or a salt thereof, that promotes the function of the polypeptide of the invention may be used as a medicine of low toxicity and high safety, for example, as a cell death inhibitor and as a prophylactic and/or therapeutic agent for various diseases including diseases accompanied by neuro-degeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotroplic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases. Still preferably, the compound or a salt thereof can be used as a prophylactic and/or therapeutic agent for Alzheimer's disease.

On the other hand, a compounds, or a salt thereof, that inhibits the function of the polypeptide of the invention may be used as a medicines such as a prophylactic and/or therapeutic agent for diseases resulted from excessive production of the polypeptide of the invention (e.g. cancers).

Thus, the polypeptide of the invention is useful as a reagent for screening for compounds, or salts thereof, that promote or inhibit the function of the polypeptide of the invention.

The present invention provides (1) a method for screening for compounds, or salts thereof, that promote or inhibit the activity (function) of the polypeptide of the invention (hereinafter, sometimes just referred to as the "promoter(s)" or "inhibitor(s)"), the method being characterized by using the polypeptide of the invention.

Specifically, for example:

(2) a method of screening for the promoters or inhibitors is provided, wherein cell death inhibitory activities are compared between (i) when cells are contacted with the polypeptide of the invention and (ii) when cells are contacted with the polypeptide of the invention and a test compound.

More specifically, in the above-described screening method, cells are cultured under the conditions of (i) and (ii), and then survival ratios are measured.

As the cells, those cells in which cell death may be induced are used preferably. Specific example of cells useful in the invention include, but are not limited to, rat adrenal medulla-derived pheochromocytoma cells (e.g. PC12h cells in Examples described later); rat or mouse nerve-derived cell lines transformed with a vector comprising a DNA encoding the causative gene for familial Alzheimer's disease; and primary culture of mouse cerebral cortex cells. The death of these cells is induced by addition of glutamic acid, removal of serum, addition of β amyloid protein, or expression of the integrated DNA encoding the causative gene of familial Alzheimer's disease.

The medium may be any medium as long as it does not inhibit the cell death inhibitory effect of the polypeptide of the invention. For example, Dulbecco's modified Eagle's medium (DMEM) may be used.

Survival ratios may be measured by known methods, e.g., a method in which the lactate dehydrogenase (LDH) activity in cell extract is measured; MTT (3-(4,5-dimethyl-2-thiazolyl)-2,5-diphenyl-2H-tetrazolium bromide) assay; MTS (3-(4,5-dimethylthiazol-2-yl)-5-(3-carboxymethoxyphenyl)-2-(4-sulfophenyl)-2H-tetrazolium) assay; trypan blue staining; or Calcein staining (Proc. Natl. Acad. Sci. USA 98: 6336–6341, 2001; NeuroReport 13:903–907, 2002; WO 01/21787).

The test compound may be, for example, a peptide, protein, non-peptidic compound, synthetic compound, fermentation product, cell extract, plant extract, or animal tissue extract. These compounds may be either novel compounds or known compounds.

For example, a test compound which promotes the cell death inhibitory activity (e.g. survival ratio) in (ii) above by about 20% or more, preferably by about 30% or more, more preferably by about 50% or more compared to the activity in (i) above may be selected as a compound, or a salt thereof, that promotes the activity of the polypeptide of the invention.

For example, a test compound which inhibits the cell death inhibitory activity (e.g. survival ratio) in (ii) above by about 20% or more, preferably by about 30% or more, more preferably by about 50% or more compared to the activity in (i) above may be selected as a compound, or a salt thereof, that inhibits the activity of the polypeptide of the invention.

The polynucleotide of the invention is useful as a reagent for screening for compounds, or salts thereof, that promote or inhibit the expression of the polypeptide gene of the invention.

The present invention provides (3) a method of screening for compounds, or salts thereof, that promote or inhibit the expression of the polypeptide gene of the invention (hereinafter, sometimes just referred to as the "promoter(s)" or "inhibitor(s)"), the method being characterized by using the polypeptide of the invention. More specifically, for example:

(4) a method of screening for the promoters or inhibitors is provided, wherein the two cases of (iii) a cell capable of producing the polypeptide of the invention is cultured and (iv) a mixture of the cell capable of producing the polypeptide of the invention and a test compound is cultured are compared.

In the above-described screening method, for example, the expression levels of the polypeptide gene of the invention (e.g. enzyme activities of alkali phosphatase, luciferase, etc. inserted downstream of the promoter for the polypeptide gene of the invention; or levels of mRNA encoding the polypeptide of the invention) are measured and compared.

Specific examples of cells capable of producing the polypeptide of the invention include, but are not limited to, hosts (transformants) transformed with a vector comprising a DNA encoding the polypeptide of the invention. As the host, animal cells such as CHO cells may be used preferably. For the screening, those transformants are used preferably which produce the polypeptide of the invention within cells or in the culture supernatant when cultured as described above. More preferably, those transformants are used in which a gene encoding secretory alkali phosphatase, luciferase or the like is inserted downstream of the promoter for the polypeptide gene of the invention.

The test compound may be, for example, a peptide, protein, non-peptidic compound, synthetic compound, fermentation product, cell extract, plant extract, or animal tissue extract. These compounds may be either novel compounds or known compounds.

In order to practice the above-described screening method, cells capable of producing the polypeptide of the invention are prepared by culturing in a medium suitable for screening.

The medium may be any medium as long as it does not inhibit the cell death inhibitory effect of the polypeptide of the invention. For example, DMEM may be used.

Expression levels of the polypeptide gene of the invention may be determined by measuring the enzyme activity of alkali phosphatase, luciferase or the like inserted downstream of the promoter for the polypeptide gene of the invention, by conventional methods.

Alternatively, expression levels of the polypeptide gene of the invention may also be measured by known methods such as Northern blotting, reverse transcription-polymerase chain reaction (RT-PCR), real time PCR analysis system (ABI; TaqMan polymerase chain reaction), or methods based thereon.

For example, a test compound which promotes the expression of the polypeptide gene of the invention in (iv) above by about 20% or more, preferably by about 30% or more, more preferably by about 50% or more compared to the expression in (iii) above may be selected as a compound, or a salt thereof, that promotes the expression of the polypeptide gene of the invention.

For example, a test compound which inhibits the expression of the polypeptide gene of the invention in (iv) above by about 20% or more, preferably by about 30% or more, more preferably by about 50% or more compared to the expression in (iii) above may be selected as a compound, or a salt thereof, that inhibits the expression of the polypeptide gene of the invention.

The polynucleotide of the invention is also useful as a reagent for screening for compounds, or salts thereof, that promote or inhibit the activity of the polypeptide gene of the invention.

The present invention provides (5) a method of screening for compounds, or salts thereof, that promote or inhibit the activity of the polypeptide of the invention (hereinafter, sometimes just referred to as the "promoter(s)" or "inhibitor(s)"), the method being characterized by using the polynucleotide of the invention.

Specifically, for example:

(6) a method of screening for promoters or inhibitors of the cell death inhibitory activity of the polypeptide of the invention is provided, wherein the two cases of (v) a cell capable of producing the polypeptide of the invention is cultured in contact with another cell and (vi) a mixture of the cell capable of producing the polypeptide of the invention and a test compound is cultured in contact with another cell are compared to thereby compare the activity of the polypeptide to inhibit the death of the another cell.

In the above screening methods, the cells are cultured under the conditions of (v) and (vi) above, and then survival ratios thereof are measured.

As the cell capable of producing the polypeptide of the invention, the cells mentioned in (4) above may be used. As the another cell, the cells mentioned in (2) above may be used. The test compound, culturing method, method for measuring cell death inhibitory activities are as described in (2) above.

For example, a test compound which promotes the cell death inhibitory activity (e.g. survival ratio) in (vi) above by about 20% or more, preferably by about 30% or more, more preferably by about 50% or more compared to the activity in (v) above may be selected as a compound, or a salt thereof, that promotes the activity of the polypeptide of the invention.

For example, a test compound which inhibits the cell death inhibitory activity (e.g. survival ratio) in (vi) above by about 20% or more, preferably by about 30% or more, more preferably by about 50% or more compared to the activity in (v) above may be selected as a compound, or a salt thereof, that inhibits the activity of the polypeptide of the invention.

The present invention provides (7) a method of screening for compounds, or salts thereof, that promote or inhibit the expression (production) of the polypeptide of the invention (hereinafter, sometimes just referred to as the "promoter(s)" or "inhibitor(s)"), the method being characterized by using the antibody of the invention.

Specifically, for example:

(8) a method of screening for promoters or inhibitors is provided, wherein the two cases of (vii) a cell capable of producing the polypeptide of the invention is cultured and (viii) a mixture of the cell capable of producing the polypeptide of the invention and a test compound is cultured are compared using the antibody of the invention.

In the above-described screening method, for example, the yields of the polypeptide of the invention in (vii) and (viii) are measured and compared using the antibody of the invention.

The test compound may be, for example, a peptide, protein, non-peptidic compound, synthetic compound, fermentation product, cell extract, plant extract, or animal tissue extract. These compounds may be either novel compounds or known compounds.

In order to practice the above-described screening method, cells capable of producing the polypeptide of the invention are cultured in a medium suitable for screening. Any medium may be used as long as it does not inhibit the production of the polypeptide of the invention. For example, DMEM may be used.

Specific examples of cells capable of producing the polypeptide of the invention include, but not limited to, hosts (transformants) transformed with a vector comprising a DNA encoding the polypeptide of the invention. As the host, animal cells such as CHO cells may be used preferably. For the screening, those transformants are used preferably which produce the polypeptide of the invention within cells or in the culture supernatant when cultured as described above.

The yields of the polypeptide of the invention may be measured by conventional methods, e.g. Western analysis of the polypeptide contained in cell extract using an antibody that recognizes the polypeptide, ELISA, or methods based thereon.

For example, a test compound which increases the yield of the polypeptide of the invention (expression level) (viii) above by about 20% or more, preferably by about 30% or more, more preferably by about 50% or more compared to the yield in (vii) above may be selected as a compound, or a salt thereof, that promotes the expression of the polypeptide of the invention.

For example, a test compound which decreases the yield of the polypeptide of the invention (expression level) (viii) above by about 20% or more, preferably by about 30% or more, more preferably by about 50% or more compared to the yield in (vii) above may be selected as a compound, or a salt thereof that inhibits the expression of the polypeptide of the invention.

The screening kit of the invention contains the polypeptide of the invention or a salt thereof.

Compounds or salts thereof obtainable by using the screening method or screening kit of the invention are compounds that are selected from peptides, proteins, non-peptidic compounds, synthetic compounds, fermentation products, cell extracts, plant extracts, animal tissue extracts, plasma and so forth. They promote or inhibit the function of the polypeptide of the invention, the expression of the polypeptide gene of the invention, or the expression of the polypeptide of the invention.

As salts of such compounds, the same salts as described earlier on the salts of the polypeptide of the invention may be used.

The compound or salt thereof that promotes the function of the polypeptide of the invention; the compound or salt thereof that promotes the expression of the polypeptide gene of the invention; or the compound or salt thereof that promotes the expression of the polypeptide of the invention each obtainable by the screening method or with the screening kit of the invention, can be used as a medicine of low toxicity and high safety, for example as a cell death inhibitor, and as a prophylactic and/or therapeutic agent for various diseases including diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases. Preferably, the compound or a salt thereof may be used as a prophylactic and/or therapeutic agent for neurodegenerative diseases and brain dysfunctions. More preferably, the compound or a salt thereof may be used as a prophylactic and/or therapeutic agent for Alzheimer's disease.

On the other hand, the compound or salt thereof that inhibits the function of the polypeptide of the invention; the compound or salt thereof that inhibits the expression of the polypeptide gene of the invention; or the compound or salt thereof that inhibits the expression of the polypeptide of the invention can be used as a medicine, for example, as a prophylactic and/or therapeutic agent for diseases resulted from excessive production of the polypeptide of the invention (e.g. cancers).

When a compound obtainable by using the screening method or screening kit of the invention is used as the above-described therapeutic and/or prophylactic agent, the compound may be used by conventional means. For example, the compound may be formulated into tablets, capsules, elixirs, microcapsules, aseptic solutions, suspensions, etc. in the same manner as described for the medicine comprising the polypeptide of the invention.

Thus obtained preparations are safe and of low toxicity, so they can be administered to mammals (e.g. human, rat, mouse, guinea pig, rabbit, sheep, pig, bovine, horse, cat, dog, monkey, etc.).

Dose levels of these compounds or salts thereof may vary depending upon their effect, the target disease, the patient to be treated, administration route, and so on. For example, when a compound that promotes the activity or function of the polypeptide of the invention is administered orally for treating Alzheimer's disease, generally the compound is administered to adult patients (60 kg in body weight) at a dose of about 0.1–100 mg/day, preferably about 1.0–50 mg/day, more preferably about 1.0–20 mg/day. With respect to parenteral administration, when a compound that promotes the activity or function of the polypeptide of the invention is administered to adult patients (60 kg in body weight) in the form of an injection for treating Alzheimer's disease, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, etc. For other animals, corresponding doses may be administered after conversion of the above-mentioned values per 60 kg based on actual body weights.

On the other hand, when a compound that inhibits the activity or function of the polypeptide of the invention is administered orally, generally the compound is administered to adult patients (60 kg in body weight) at a dose of about 0.1–100 mg/day, preferably about 1.0–50 mg/day, more preferably about 1.0–20 mg/day. With respect to parenteral administration, a compound that inhibits the function of the polypeptide of the invention is administered to adult patients (60 kg in body weight) in the form of an injection, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, etc. For other animals, corresponding doses may be administered after conversion of the above-mentioned values per 60 kg based on actual body weights.

(3) Quantitative Determination of the Polypeptide Using the Antibody of the Invention Since the antibody of the invention can specifically recognize the polypeptide of the invention, the antibody may be used for quantitative determination of the polypeptide of the invention contained in sample solutions, in particular, in quantitative determination by sandwich immunoassay.

The present invention provides:
(i) a method of quantitative determination of the polypeptide of the invention in a sample solution, comprising competitively reacting the antibody of the invention with the sample solution and the polypeptide of the invention labeled, and determining the ratio of the, labeled polypeptide of the invention bound to the antibody; and
(ii) a method of quantitative determination of the polypeptide of the invention in a sample solution, comprising reacting the sample solution with the antibody of the invention insolubilized on a carrier and another antibody of the invention labeled, simultaneously or in succession and determining the activity of the labeling agent on the insolubilized carrier.

Further, the monoclonal antibody of the invention may be used to quantitatively determine the polypeptide of the invention or may be used for detection of the polypeptide by tissue staining. For these purposes, either antibody molecules per se or the $F(ab')_2$, Fab' or Fab fragment thereof may be used.

Methods of quantitative determination of the polypeptide of the invention using the antibody of the invention are not particularly limited. Any measuring method may be used in which the amount of antibody, antigen or antibody-antigen complex corresponding to the amount of the antigen in a sample solution (e.g. the amount of the polypeptide of the invention) is detected by chemical or physical means, and then calculated from a standard curve prepared with a standard solution containing a known amount of the antigen. For example, nephrometry, competitive methods, immunometric methods and sandwich assay may be used conveniently and, in terms of sensitivity and specificity, the sandwich assay described later is particularly preferred.

Examples of labeling agents useful in measuring methods utilizing labeling substances include radioisotopes, enzymes, fluorescent substances, and luminescent substances. Examples of radioisotopes include $[^{125}I]$, $[^{131}I]$, $[^{3}H]$ and $[^{14}C]$. Preferred examples of enzymes are those which are stable and with high specific activity, e.g., β-galactosidase, β-glucosidase, alkali phosphatase, peroxidase and malate dehydrogenase. Examples of fluorescent substances include fluorescamine and fluorescein isothiocyanate. Examples of luminescent substances include luminol, luminol derivatives, luciferin, and lucigenin. Further, a biotin-avidin system may also be used for binding an antibody or antigen with a labeling agent.

Insolubilization of antigens or antibodies may be performed by physical adsorption or by chemical binding usually used for insolubilizing or immobilizing polypeptides or enzymes. Examples of carriers useful for this purpose include insoluble polysaccharides such as agarose, dextran and cellulose; synthetic resins such as polystyrene, polyacrylamide and silicone; and glass.

In the sandwich assay, a sample solution is reacted with an insolubilized monoclonal antibody of the invention (primary reaction); then, another monoclonal antibody of the invention that is labeled is reacted therewith (secondary reaction); and the activity of the labeling agent on the insolubilized carrier is measured to thereby quantitatively determine the amount of the polypeptide of the invention in the sample solution. The primary reaction and the secondary reaction may be conducted in the reverse order, or they may be conducted simultaneously or with an interval. The type of the labeling agent and the method of insolubilization may be the same as those described herein earlier. In immunoassays using the sandwich technique, the antibody insolubilized on a solid phase or the antibody labeled is not necessarily a single antibody; a mixture of two or more antibodies may be used for the purposes of enhancing the sensitivity of measurement, etc.

In the method of measuring the polypeptide of the invention by the sandwich assay of the invention, the monoclonal antibodies of the invention used in the primary and the secondary reactions are preferably those antibodies whose sites of binding to the polypeptide of the invention are different from each other. For example, if the antibody used in the secondary reaction recognizes the C-terminal region of the polypeptide of the invention, an antibody that recognizes a site other than the C-terminal region, e.g. an N-terminal region, is preferably used in the primary reaction.

The monoclonal antibody of the invention may be used in a measuring system other than the sandwich assay, such as competitive methods, immunometric methods and nephrometry.

Incompetitive methods, an antigen in a sample solution and a labeled antigen are reacted competitively with an antibody; then, unreacted labeled antigen (F) and labeled antigen bound to the antibody (B) are separated (i.e. B/F separation); and the amount of the label of B or F is measured to thereby quantitatively determine the amount of the antigen in the sample solution. With respect to this reaction method, there are a liquid phase method in which a soluble antibody is used; and the B/F separation is conducted with polyethylene glycol, and a second antibody to the above-mentioned antibody is used; and a solid phase method in which a solidified antibody is used as the first antibody or a soluble antibody is used as the first antibody while a solidified antibody is used as the second antibody.

In immunometric methods, an antigen in a sample solution and a solidified antigen are reacted competitively with a specific amount of a labeled antibody, followed by separation of the solid phase from the liquid phase; or an antigen in a sample solution is reacted with an excessive amount of a labeled antibody, and then a solidified antigen is added to bind unreacted labeled antibody to the solid phase, followed by separation of the solid phase from the liquid phase. Subsequently, the amount of label in one of the phases is measured to determine the amount of the antigen in the sample solution.

In nephrometry, the amount of insoluble precipitate generated as a result of antigen-antibody reaction in a gel or solution is measured. Even when the amount of the antigen in a sample solution is small and thus only a small amount of such precipitate is obtained, laser nephrometry utilizing the scattering of laser can be used conveniently.

In applying each of those immunological measuring methods to the measuring method of the present invention, no special conditions or operations are required. A measuring system for the polypeptide of the present invention may be constructed using the conventional conditions and operational procedures in the relevant measuring method while taking into account usual technical consideration of those skilled in the art. For details of these commonly used technical means, a variety of reviews, reference books, etc. may be referred to.

For example, Hiroshi Irie (ed.): "Radioimmunoassay" (Kodansha, 1974); Hiroshi Irie (ed.): "Radioimmunoassay; Second Series" (Kodansha, 1979); Eiji Ishikawa et al. (ed.): "Enzyme Immunoassay" (Igaku Shoin, Japan, 1978); Eiji Ishikawa et al. (ed.): "Enzyme Immunoassay" (Second Edition) (Igaku Shoin, 1982); Eiji Ishikawa et al. (ed.): "Enzyme Immnunoassay" (Third Edition) (Igaku Shoin, 1987); "Methods in Enzymology", Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part 1: Hybridoma Technology and Monoclonal Antibodies)) (Academic Press) and the like may be referred to.

By using the antibody of the invention as described above, the polypeptide of the invention can be quantitatively determined with high sensitivity.

Further, when an increase or decrease is detected in the concentration of the polypeptide of the invention in a subject by quantitatively determining the concentration of the polypeptide of the invention using the antibody of the invention, it is possible to diagnose that the subject has one of the following diseases: for example, diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subaraclinoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases; or that the subject is very likely to develop such a disease in the future.

Further, the antibody of the invention may be used for detecting the polypeptide of the invention present in body fluids, tissues or other samples. The antibody of the invention may also be used in the preparation of antibody columns for use in the purification of the polypeptide of the invention; in the detection of the polypeptide of the invention in individual fractions generated in the course of purification; and in the analysis of the behavior of the polypeptide of the invention in test cells.

(4) Diagnostic Agents Comprising the Polynucleotide of the Invention

The polynucleotide of the invention can, when used as a probe for example, detect mutativeities in DNA or mRNA encoding the polypeptide of the invention (gene mutativeities) in mammals (e.g. human, rat, mouse, guinea pig, rabbit, sheep, pig, bovine, horse, cat, dog, monkey, etc.). Thus, the polynucleotide of the invention is useful as a gene diagnostic for diagnosing, e.g., damage, mutations or reduced expression of the above DNA or mRNA, or increase or excessive expression of the above DNA or mRNA.

Gene diagnosis using the polynucleotide of the invention may be performed by known methods such as Northern hybridization or PCR-SSCP method (Genomics, Vol. 5, 874–879 (1989); Proceedings of the National Academy of Sciences of the USA, 86: 2766–2770 (1989)).

When a decrease in expression is detected by Northern hybridization or when a mutation(s) is/are detected in the DNA by PCR-SSCP method, for example, it is possible to diagnose that the relevant subject is very likely to have one of the following diseases: for example, diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases.

(5) Medicines and Diagnostic Agents Containing Antisense Polynucleotide

Antisense polynucleotide that complementarily binds to the polynucleotide of the invention and thus inhibits the expression of that polynucleotide can inhibit the function of the polypeptide or the polynucleotide of the invention in vivo. Therefore, the antisense polynucleotide may be used as prophylactic and/or therapeutic agents for diseases resulted from excessive expression of the polypeptide of the invention (e.g. cancers).

The above-mentioned antisense polynucleotide may be used as the above-mentioned prophylactic and/or therapeutic agents in the same manner as the various prophylactic and/or therapeutic agents containing the polynucleotide of the invention described earlier.

For example, the antisense polynucleotide per se or the antisense polynucleotide inserted into an appropriate vector such as a retrovirus vector, adenovirus vector, adeno-associated virus vector, etc. may be administered using conventional means. The antisense polynucleotide may be administered as it is or after formulation with physiologically acceptable carriers such as adjuvants to promote uptake, by means of a gene gun or a catheter such as hydrogel catheter.

Further, the antisense polynucleotide may be used as an oligonucleotide probe for diagnostic purposes to examine the presence or state of expression of the polynucleotide of the invention in tissues or cells. The antisense polynucleotide may be used for diagnosis of, for example, diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotroplhic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subaracloid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases-and endocrine diseases.

(6) Medicines Containing the Antibody of the Invention

The antibody of the invention that has an effect of neutralizing the activity of the polypeptide of the invention may be used as prophylactic and/or therapeutic agents for diseases resulted from excessive expression of the polypeptide of the invention (e.g. cancers).

The above-mentioned prophylactic and/or therapeutic agents comprising the antibody of the invention may be administered orally or parenterally to mammals (e.g. human, rat, rabbit, sheep, pig, bovine, cat, dog, monkey, etc.) in the forms of liquid preparations without any processing or in appropriate forms of pharmaceutical compositions. Dose levels may vary depending upon the patient to be treated, the target disease, symptoms, administration route, and so on. However, it is convenient to inject the antibody of the invention intravenously at a dose of about 0.01–20 mg/kg body weight, preferably about 0.1–10 mg/kg body weight, more preferably about 0.1–5 mg/kg body weight per administration about one to five times a day, preferably about one to three times a day. In other parenteral administration and oral administration, similar dose levels may be used. If symptoms are particularly heavy, the dose may be increased accordingly.

The antibody of the invention may be administered per se or in the forms of appropriate pharmaceutical compositions. The pharmaceutical compositions for the above administration comprise the antibody or salt thereof, pharmacologically acceptable carriers, and diluents or excipients. Such compositions are provided in forms appropriate for oral or parenteral administration.

For example, compositions for oral administration include solid or liquid preparations such as tablets (including sugar-coated tablets and film-coated tablets), pills, granules, dispersants, capsules (including soft capsules), syrups, emulsions and suspensions. These compositions are prepared according to conventional methods and contain carriers, diluents or excipients conventionally used in the field of medicine manufacturing. For example, lactose, starch, sucrose, magnesium stearate and the like are used as carriers or excipients for tablets.

Compositions for parenteral administration include, for example, injections and suppositories. Injections include intravenous injections, subcutaneous injections, intradermal injections, muscle injections, instilment injections, etc. Such injections may be prepared by dissolving, suspending or emulsifying the above antibody or salt thereof in an aseptic, aqueous or oily liquid. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nontionic surfactant [e.g. Polysorbate 80™, HCO-50 (polyoxyethylene (50 mol) adduct of hydrogenated castor oil)], etc.). Examples of oily liquids for injection include sesame oil and soybean oil. They may be used in combination with an auxiliary solubilizer such as benzyl benzoate, benzyl alcohol, etc. Usually, the prepared injections are filled in appropriate ampoules. Suppositories for administration into rectum may be prepared by mixing the antibody or a salt thereof with a conventional suppository base.

It is convenient to formulate the above-described pharmaceutical compositions for oral or parenteral administration into unlit dosage forms that would give an appropriate dose of the active ingredient. Examples of such unit dosage forms include tablets, pills, capsules, injections (ampoules), and suppositories. Usually, each unit of these dosage forms contains preferably about 5–500 mg of the above-described antibody. In particular, each unit contains preferably about 5–100 mg in injections, and each unit in other dosage forms contains preferably about 10–250 mg.

The above-described pharmaceutical compositions may contain other active ingredients as long as they do not produce undesirable interaction with the above-described antibody.

(7) DNA-Transferred Animals

The present invention further provides non-human mammals harboring a foreign DNA coding for the polypeptide of the invention (hereinafter referred to briefly as the "foreign DNA of the invention") or a mutant thereof (sometimes referred to briefly as the "foreign mutant DNA of the invention").

Thus, the present invention provides:
(1) A non-human mammal harboring the foreign DNA of the invention or a mutant DNA thereof:
(2) The non-human mammal according to (1) which is a rodent:
(3) The non-human mammal according to (2) wherein the rodent is mouse or rat; and
(4) A recombinant vector containing the foreign DNA of the invention or a mutant DNA thereof and capable of expressing the DNA in a mammal.

The non-human manual harboring the foreign DNA of the invention or a mutant DNA thereof (hereinafter referred to briefly as the "DNA-transferred animal of the invention") can be created by transferring the DNA of interest to a germinal cell such as unfertilized egg cells, fertilized egg cells, or sperm cells or primordial cells thereof, preferably during the period of embryogenesis in the ontogenesis of the non-human mammal (more preferably, in the stage of a single cell or a fertilized egg cell and generally at the 8-cell stage or earlier), by the calcium phosphate method, electric pulse method, lipofection method, agglutination method, microinjection method, particle gun method, or DEAE-dextran method. It is also possible to transfer the foreign DNA of the invention of interest into somatic cells, organs in the living body, tissue cells, or the like by such DNA transfer methods to use the resultant cells or tissues in cell culture or tissue culture. Further, by fusing the resultant cells with the above-mentioned germinal cell by known cell fusion methods, it is also possible to create the DNA-transferred animal of the invention.

The non-human manual useful in the invention includes bovine, pig, sheep, goat, rabbit, dog, cat, guinea pig, hamster, mouse, rat, and so on. From the viewpoint of construction of diseased animal models, rodents which have comparatively short ontogenesis and life cycles and can be easily bred, particularly mouse (e.g. pure strains such as C57BL/6, DBA2, etc. and hybrid strains such as B6C3F$_1$, BDF$_1$, B6D2F$_1$, BALB/c, ICR, etc.) or rat (e.g. Wistar, SD, etc.), are preferred.

As the "mammal" in the expression "a recombinant vector . . . capable of expressing the DNA in a mammal", human may also be enumerated in addition to the above-mentioned non-human mammals.

The foreign DNA of the invention is not a DNA of the invention which is inherently possessed by the non-human mammal, but a DNA of the invention that has been once isolated and extracted from a mammal.

Examples of the mutant DNAs of the invention include not oily the DNAs that have variations (e.g. mutations) in the nucleotide sequence of the original DNA of the invention as a result of, for example, addition or deletion of nucleotides or substitution with other nucleotides, but also mutative DNAs.

The term "mutative DNA" as used herein means any DNA that causes expression of a mutative polypeptide of the invention. For example, a DNA that allows expression of a polypeptide that inhibits the function of the normal polypeptide of the invention may be used.

The foreign DNA of the invention may be derived from a mammal that is of the same species as that of the host animal or of different species. For transferring of the DNA of the invention to the host animal, it is generally advantageous to use a DNA construct in which the DNA is ligated downstream of a promoter capable of expressing the DNA in animal cells. For example, in transferring the human DNA of the invention, this human DNA of the invention may be ligated downstream of a promoter capable of directing expression of DNAs derived from various animals (e.g. rabbit, dog, cat, guinea pig, hamster, rat, mouse, etc.) harboring the DNA of the invention having high homology to the human DNA to thereby prepare a DNA construct (e.g. vector), which can then be microinjected into fertilized egg cells of a host manual such as fertilized mouse egg cells. Thus, a DNA-transferred manual showing high expression of the DNA of the invention can be created.

Examples of the expression vector for the polypeptide of the invention include plasmids derived from *E. coli*, plasmids derived from *B. subtilis*, plasmids derived from yeast, λ phage and other bacteriophages, retroviruses such as Molony leukemia virus, and animal viruses such as vaccinia virus and vaculovirus. Preferable examples are *E. coli*-derived plasmids, *B. subtilis*-derived plasmids and yeast-derived plasmids.

Examples of promoters that regulate the expression of the DNA include (1) promoters for DNAs derived from viruses (e.g. simian virus, cytomegalovirus, Molony leukemia virus, JC virus, papilloma virus, poliovirus, etc.), (2) promoters derived from mammals (e.g. human, rabbit, dog, cat, guinea pig, hamster, rat, mouse, etc.), for example, promoters of albumin, insulin II, uroprakin II, elastase, erythropoietin, endothelin, muscle creatine kinase, glial fibrillary acidic protein, glutathione S-transferase, platelet-derived growth factor β, keratin K1, K10, and K14, collagen type I and type II, cyclic AMP-dependent polypeptide kinase βI subunit, dystrophin, tartaric acid-resistant alkaline phosphatase, atrial natriuretic factor, endothelial receptor tyrosine kinase (generally abbreviated to Tie2), sodium/potassium-dependent adenosine triphosphatase (Na, K-ATPase), neurofilament light chain, metallothionein I and IIA, metalloproteiniase I tissue inhibitor, MHC Class I antigen (H-2L), H-ras, renin, dopamine β-hydroxylase, thyroid peroxidase (TPO), polypeptide chain elongation factor 1α (EF-1α), β-actin, α- and β-myosin heavy chain, myosin light chains 1 and 2, myelin basic protein, thyroglobulin, Thy-1, immunoglobulin H chain variable region (VNP), serum amyloid P component, myoglobin, troponin C, smooth muscle α-actin, pre-proenkephalin A, vasopressin, and so on. Preferable are those promoters which can direct high expression of the DNA in the whole body, e.g. cytomegalovirus promoter, human polypeptide chain elongation factor 1α (EF-1α) promoter and human and chicken β-actin promoters.

It is preferable that the vector has a sequence for terminating the transcription of the mRNA of interest (generally called terminator) in the DNA-transferred mammal. For example, sequences derived from viruses or various mammals may be used. Preferably, SV40 terminator derived from simian virus or the like is used.

In addition, for enhancing the expression of the DNA of interest further, it is possible, depending on the specific purpose, to ligate a splicing signal, an enhancer domain, a portion of an eucaryotic DNA intron, etc. upstream of the 5'-end of the promoter region, between the promoter region and the translated region, or downstream of the 3'-end of the translated region.

The translated region can be prepared as a DNA construct which can be expressed in a DNA-transferred animal, by conventional recombinant DNA techniques, i.e. by ligating it downstream of the promoter and, if desired, upstream of the transcription termination site.

The transfer of the foreign DNA of the invention at the fertilized egg cell stage insures that the DNA will be ubiquitous in all the germ cells and somatic cells of the host mammal. The presence of the DNA of the invention in the germ cells of the DNA-transferred animal following DNA transfer means that all the germinal cells and somatic cells of all the subsequent generations of the DNA-transferred animal harbor the DNA of the invention. Thus, the progeny of such DNA-transferred animal which inherited the foreign DNA of the invention have the DNA in all of their germ cells and somatic cells.

The non-human mammal harboring the foreign normal DNA of the invention can be verified by mating to retain the foreign DNA stably and then bred as a line harboring that DNA from generation to generation under usual breeding conditions.

The transfer of the foreign DNA of the invention at the fertilized egg cell stage insures that the DNA will be present in excess in all the germ cells and somatic cells of the host mammal. The presence of the foreign DNA of the invention in the germ cells of the DNA-transferred animal following the DNA transfer means that all the germinal cells and somatic cells of all the progeny of the DNA-transferred animal harbor the foreign DNA of the invention in excess. Thus, the progeny of such DNA-transferred animal which inherited the foreign DNA of the invention have the DNA in excess in their germ cells and somatic cells.

By preparing homozygous animals having the transferred DNA in both homologous chromosomes and mating male animals with female animals, it is possible to breed through generations so that every progeny harbors the DNA in excess.

The non-human mammal harboring the normal DNA of the invention features a high expression of the normal DNA and may eventually develop a hyperergasia of the polypeptide of the invention though activation of the function of the endogenous normal DNA. Thus, the animal can be utilized as an animal model of that disease. For example, by using the DNA-transferred animal harboring the normal DNA of the invention, it is possible to study the hyperergasia of the polypeptide of the invention, to elucidate the mechanisms of diseases with which the polypeptide of the invention is associated, and to explore therapeutic modalities for the diseases.

Furthermore, the mammal to which the foreign normal DNA of the invention has been transferred presents symptoms due to an increase in the free polypeptide of the invention and, therefore, can also be used in the screening of therapeutic drugs for diseases with which the polypeptide of the invention is associated.

On the other hand, the non-human mammal harboring the foreign mutative DNA of the invention can be verified by mating to retain the DNA stably and then bred as a line harboring the DNA from generation to generation under usual breeding conditions. Moreover, it is possible to incorporate the foreign DNA of interest in the above-mentioned plasmid and use it as a starting material. The DNA construct with the promoter can be prepared by conventional recombinant DNA techniques. Transfer of the mutative DNA of the invention in the fertilized egg cell stage insures that the transferred DNA will be ubiquitous in all the germ cells and somatic cells of the host mammal. The presence of the mutative DNA of the invention in the germ cells of the DNA-transferred animal means that all the progeny of this DNA-transferred animal harbor the mutative DNA of the invention in all of their germinal cells and somatic cells. The progeny of this animal harbor the mutative DNA of the invention in all of their germinal cells and somatic cells. By preparing homozygous male and female animals having the introduced DNA in both homologous chromosomes and mating them, it can be insured that every progeny harbors the DNA from generation to generation.

The non-human manual harboring the mutative DNA of the invention features a high expression of the mutative DNA and, therefore, may eventually develop adiaphoria associated with functional inactivation of the polypeptide of the invention through inhibition of the function of the endogenous normal DNA. Thus, the animal can be utilized as an animal model of that disease. For example, by using the DNA-transferred animal harboring the mutative DNA of the invention, analysis of the mechanism of this functional inactivation adiaphoria attributable to the polypeptide of the invention and therapeutic modalities for the disease can be explored.

As a specific potential use, the DNA-transferred animal with a high expression of the mutative DNA of the invention can be used as a model for elucidating the functional inhibition of the normal polypeptide by the mutative polypeptide of the invention (dominant negative effect) in adiaphoria of functional inactivation.

Moreover, the DNA-transferred mammal harboring the foreign mutative DNA of the invention develops symptoms due to an increase in the free polypeptide of the invention and, therefore, can be utilized in the screening of therapeutic drugs for adiaphoria attributable to functional inactivation of the polypeptide of the invention.

As other potential uses of the two types of DNA-transferred animals harboring the two kinds of DNAs of the invention, the following may be considered:
(1) Use as a cell source for tissue culture;
(2) Analysis of those genes or polypeptides which are expressed or activated or deactivated specifically by the polypeptide of the invention, by comparing and analyzing the DNA or RNA in tissues of the DNA-transferred animal of the invention with the DNA or RNA of non-DNA-transferred animal (control animal) or by comparing and analyzing the compositions of the polypeptides expressed;
(3) Study of the functions of cells of those tissues which are generally difficult to culture, by using the cells from the tissues containing the DNA as cultured by the standard tissue culture technique;
(4) Screening for drugs capable of enhancing the cell functions by using the cells described in (3); and
(5) Isolation and purification of the mutant polypeptide of the invention and construction of antibodies thereto.

Furthermore, by using the DNA-transferred animal of the invention, clinical symptoms of diseases associated with the polypeptide of the invention, inclusive of above-described adiaphoria associated with functional inactivation of the polypeptide of the invention, can be investigated. In addition, more detailed pathological findings can be obtained in various organs of this model of diseases associated with the polypeptide of the invention, thus contributing to the development of new therapies as well as the study and treatment of secondary diseases arising from such diseases.

Moreover, by removing various organs from the DNA-transferred animal of the invention, mincing them and digesting them with a proteolytic enzyme such as trypsin, free single cells harboring the transferred DNA can be recovered. These cells can be cultured for establishment of a cell line. Furthermore, characterization of cells producing the polypeptide of the invention can be made and their relationship with apoptosis, differentiation, or proliferation, the mechanism of signal transduction in them, and mutativeities involved can be explored to thereby generate information useful for further elucidation of the polypeptide of the invention and its effects.

Moreover, for the development of therapeutic drugs for diseases associated with the polypeptide of the invention, such as adiaphoria resulted from functional inactivation of the polypeptide of the invention by using the DNA-transferred animal of the invention, an effective and rapid screening technology for such therapeutic drugs can be established by using the test and assay methods described hereinbefore. In addition, by using the above DNA-transferred animal or the foreign DNA expression vector of the invention, gene therapies for diseases associated with the polypeptide of the invention can be explored and developed.

(8) Knockout Animals

The invention further provides non-human-mammalian embryonic stem cells wherein the DNA of the invention is inactivated, and non-human mammals deficient in expression of the DNA of the invention wherein the DNA of the invention is deactivated.

The invention, therefore, provides:
(1) A non-human mammalian embryonic stem cell wherein the DNA of the invention is inactivated;
(2) The embryonic stem cell according to in (1) wherein the DNA is inactivated by introduction of a reporter gene (e.g. *E. coli*-derived β-galactosidase gene);
(3) The embryonic stem cell according to (1) which is neomycin-resistant;
(4) The embryonic stem cell according to (1) wherein the non-human mammal is a rodent;
(5) The embryonic stem cell according to (4) wherein the rodent is mouse;
(6) A non-human mammal deficient in expression of the DNA of the invention, wherein the DNA is inactivated;
(7) The nonhuman mammal according to (6) wherein the DNA is inactivated by introduction of a reporter gene (e.g. *E coli*-derived β-galactosidase gene) and the reporter gene can be expressed under the control of the promoter for the DNA of the invention;
(8) The non-human mammal according to (6) wherein the non-human mammal is a rodent;
(9) The non-human mammal according to (8) wherein the rodent is mouse; and
(10) A method for screening for compounds, or salts thereof, that enhance or inhibit the promoter activity for the DNA of the invention, which comprises administering a test compound to the non-human mammal according to (7) and detecting expression of the reporter gene.

The expression "non-human mammalian embryonic stem cell wherein the DNA of the invention is inactivated" means the embryonic stem cell (hereinafter referred to briefly as ES cell) of a non-human mammal in which the DNA has been deprived of the capacity to express the polypeptide of the invention (hereinafter, sometimes referred to as the "knockout DNA of the invention") through introduction of an artificial mutation to the DNA of the invention possessed by the non-human manual to thereby inhibit expression of the DNA of the invention or through substantial deprivation of the activity of the polypeptide of the invention encoded by the DNA.

As the non-human mammals, the same animals as mentioned hereinbefore may be used.

Examples of the method for introducing an artificial mutation to the DNA of the invention are a deletion of some or all of the DNA sequence, or an insertion of a different DNA, or substitution with a different DNA by the genetic engineering technology. The knockout DNA of the invention may be created by such a mutation that would shift the reading frame or destroy the function of the promoter or exon.

The non-human mammalian embryonic stem cell wherein the DNA of the invention is inactivated (hereinafter referred to as the "DNA inactivated ES cell of the invention" or the "knockout ES cell of the invention") can be prepared by, for example, procedures which comprise isolating the DNA of the invention from the desired non-human mammal, inserting a drug-resistance gene, typically neomycin-resistance gene or hygromycin-resistance gene, or a reporter gene such as lacZ (β-galactosidase gene) or cat (chloramphenicol acetyltransferase gene) into its exon region to disrupt the function of the exon or inserting a DNA sequence for terminating genie transcription (e.g. poly A addition signal) in an intron region between exons to thereby inhibit synthesis of a complete mRNA, introducing the thus-constructed DNA strand having a DNA sequence designed to eventually disrupt the gene (hereinafter, referred to briefly as the "targeting vector") into the chromosomes of the host animal by homologous recombination, subjecting the resulting ES cell to Southern hybridization analysis using a DNA sequence located on the DNA of the invention or in its vicinity as a probe or a PCR procedure using a DNA sequence located on the targeting vector and a DNA sequence in the vicinity but not including the DNA of the invention used in the construction of the targeting vector as primers, and selecting the knockout ES cell of the invention.

The original ES cell to be used for inactivation of the DNA of the invention by the homologous recombination technique or the like may be an already established cell line such as those mentioned hereinbefore or a new cell line established de novo by the known method of Evans and Kaufman. Taking mouse ES cells as an example, ES cells of the 129 line are generally used but the immunological background of this line is not clear. Therefore, the alternative cell line for preparing pure-line ES cells with an immunologically defined genetic background can be used with advantage, for example, $BDF_1$ mice created by the hybridization of C57BL/6 mice and C57BL/6 mice, both yielding few eggs, with DBA/2 mice ($BDF_1=F_1$ of C57BL/6 and DBA/2). In addition to the advantage of high egg output and sturdiness of the egg, $BDF_1$ mice have the background of C57BL/6 mice and so that in the construction of a disease model with ES cells obtained, the genetic background of the model mice can be converted to that of C57BL/6 mice by back-crossing with C57BL/6.

Moreover, in establishing an ES cell line, it is generally used blastocytes 3.5 days following fertilization but, aside from them, a large number of early embryos can be prepared with high efficiency by harvesting the embryos at the 8-cell stage and culturing them into blastocytes.

Furthermore, while ES cells can be used from both male and female animals, generally ES cells of male animals are more convenient for the construction of reproduction line chimeras. Moreover, for the purpose of reducing the burden of the complicated cultural procedure, it is preferable to carry out sexing as early as possible.

As a typical method for sexing ES cells, there can be mentioned the method in which the gene in the sex determination region on the Y chromosome is amplified and detected by PCR. Whereas the conventional karyotype analysis requires about $10^6$ cells, the above method requires only about one colony equivalent of ES cells (about 50 cells). Therefore, the primary selection of ES cells in an early stage can be made by this sexing method. Since male cells can thus be selected in the early stage, the trouble in the initial stage of culture can be drastically reduced.

Moreover, the secondary selection can be carried out by G-banding for the number of chromosomes. The number of chromosomes in the resulting ES cell is preferably 100% of the normal number but this goal may not be reached due to the physical and other factors involved in the establishment of the line. In such cases, it is preferable to knockout the gene of the ES cell and re-clone it into the normal cell (taking a mouse as an example, the cell in which the number of chromosomes is 2n=40).

The embryonic stem cell line thus established is generally very satisfactory in proliferation characteristic but since it is liable to lose its ontogenic ability, it must be subcultured with sufficient care. For example, this cell line should be cultured on suitable feeder cells such as STO fibroblasts in the presence of LIF (1–10000 U/ml) in a carbon dioxide incubator (preferably 5% $CO_2$, 95% air or 5% oxygen, 5% $CO_2$, 90% air) at about 37° C. And, in subculture, it should be treated with trypsin/EDTA solution (generally 0.001–0.5% trypsin/0.1–5 mM EDTA, preferably about 0.1% trypsin/1 mM EDTA) to provide single cells and seed them on freshly prepared feeder cells. While such subculture is generally performed every 1–3 days, it is good practice to observe the cells on each occasion and, whenever morphologically mutative cells are discovered, discard the culture.

ES cells can be allowed to differentiate into various types of cells, such as head long muscle cells, visceral muscle cells, heart muscle cells. etc. by conducting monolayer culture to a high density under suitable conditions or suspension culture until a mass of cells is formed (M. J. Evans & M. H. Kaufman, Nature, 292, 154, 1981; G. R. Martin, Proceedings of National Academy of Science USA, 78, 7634, 1981; T. C. Doetschman et al., Journal of Embryology and Experimental Morphology, 87, 27, 1985), and the cell deficient in expression of the DNA of the invention as obtainable by causing the ES cell of the invention to differentiate is useful for the cytobiological in vitro study of the polypeptide of the invention.

The nonhuman mammal deficient in expression of the DNA of the invention can be differentiated from normal animals by assaying the mRNA in the animals by the known method and comparing the amounts of expression indirectly.

As the non-human mammal used for this purpose, the same animals as mentioned hereinbefore may be used.

With respect to the non-human mammal deficient in expression of the DNA of the invention, the DNA of the invention can be knocked out by introducing the targeting vector constructed as described above into, for example, mouse embryonic stem cells or mouse egg cells and thereby allowing the DNA sequence of the targeting vector harboring the inactivated DNA of the invention to undergo homologous recombination with, and accordingly replacing, the DNA of the invention on the mouse embryonic stem cell or egg cell chromosomes.

The cell with the DNA of the invention thus knocked out can be judged by Southern hybridization analysis using a DNA sequence on the DNA of the invention or in its vicinity as a probe or by PCR using a DNA sequence on the targeting vector or a mouse-derived DNA sequence in a region adjacent to but not including the DNA of the invention used in the targeting vector as primers. When a non-human mammalian embryonic stem cell is used, a cell line with the DNA of the invention knocked out by the homologous recombination technique is cloned and injected into the non-human mammalian embryo or blastocyte at a suitable stage of embryogenesis, for example at the 8-cell stage, and the resulting chimera embryo is transplanted in the pseudopregnant uterus of the non-human mammal. The animal thus obtained is a chimera animal constituted by both the cells harboring the normal DNA locus of the invention and the cells harboring the artificially mutated DNA locus of the invention.

When some of the gametes of this chimera animal harbor the mutated DNA locus of the invention, an individual whose entire tissue is constituted by cells harboring the mutated DNA locus of the invention can be screened from the colony of animals obtained by crossing such a chimera animal with a normal animal, for example by coat color discrimination. The individuals thus selected are usually animals hetero-deficient in expression of the polypeptide of the invention and by mating such individuals hetero-deficient in expression of the polypeptide of the invention with each other, animals homo-deficient in expression of the polypeptide of the invention can be acquired.

When egg cells are used, a transgenic non-human mammal with the targeting vector having been introduced into its chromosomes can be prepared by injecting the DNA solution into the egg cell nucleus by the microinjection technique and selecting animals expressing a mutation of the DNA of the invention by homologous recombination.

The individuals with the DNA of the invention thus knocked out are mated to verify that the animals obtained by mating also have the DNA knocked out and they can be sub-bred under the usual breeding conditions.

Preparation and maintenance of the germ line may also be carried out in accordance with conventional methods. Thus, by mating male and female animals harboring the inactivated DNA, homozygotes having the inactivated DNA in both homologous chromosomes can be obtained. The homozygotes thus obtained are bred under such conditions that, with regard to the dam, the number of homozygotes is plural per normal individual. By mating male and female heterozygotes, homozygotes and heterozygotes both harboring the inactivated DNA can be sub-bread.

The non-human mammalian embryonic stem cell harboring the inactivated DNA of the invention is very useful for the construction of non-human mammals deficient in expression of the DNA of the invention.

Moreover, the mammal deficient in expression of the polypeptide of the invention lacks the various biological activities inducible by the polypeptide of the invention and can, therefore, be of use as an animal model of diseases arising from inactivation of the biological activities of the polypeptide of the invention, thus being useful in the etiological studies of such diseases and development of therapeutic methods.

(8a) Method for Screening for Compounds with Therapeutic/Prophylactic Effect upon Diseases Resulted from Deficiency of or Damage to the DNA of the Invention Non-human mammals deficient in expression of the DNA of the invention may be used for screening for compounds with a therapeutic and/or prophylactic effect upon diseases resulted from deficiency of or damage to the DNA of the invention, for example, diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases.

The present invention provides a method for screening for compounds, or salts thereof, having a therapeutic and/or prophylactic effect upon diseases resulted from deficiency of or damage to the DNA of the invention, which is characterized by administering a test compound to a non-human mammal deficient in expression of the DNA of the invention aid observing and measuring the changes in the mammal.

As the nonhuman mammal deficient in expression of the DNA of the invention, the same animals as described earlier may be used.

The test compound may be, for example, a peptide, protein, non-peptidic compound, synthetic compound, fermentation product, cell extract, plant extract, animal tissue extract or plasma. These compounds may be either novel compounds or known compounds.

Specifically, a non-human mammal deficient in expression of the DNA of the invention is treated with a test compound and then compared with a control animal not treated with the compound. Subsequently, the therapeutic and/or prophylactic effect of the test compound may be examined using the changes in individual organs, tissues or disease symptoms in the mammal as indicators.

As a method for treating a test animal with a test compound, oral administration, intravenous injection, or the like may be used. The method may be appropriately selected depending on the symptoms of the test animal, the nature of the test compound, and so on. Dose levels of the test compound may be appropriately selected taking into account of the administration method, the nature of the test compound, and so on.

Compounds obtainable by using the screening method of the invention are compounds selected from the above-mentioned test compounds, and have a therapeutic and/or prophylactic effect upon diseases resulted from deficiency of or damage to the DNA of the invention, for example, diseases accompanied by neurodegeneration, such as neurodegenerative diseases [e.g. Alzheimer 's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases. Therefore, they may be used as medicines that are safe and of low toxicity, for example as prophylactic and/or therapeutic agents for those diseases that are safe and of low toxicity. Furthermore, compounds inducible from those compounds obtained by the above screening may also be used in the same manner.

The compound obtained by the above screening may be in a salt form. As salts of the compounds, salts formed with physiologically acceptable acids (e.g. organic or inorganic acids) or bases (e.g. alkali metals) may be used. Especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

Medicines comprising the compound, or a salt thereof, obtained by the screening may be prepared in the same manner as described for medicines comprising the polypeptide of the invention.

Since the thus obtained preparations are safe and of low toxicity, they may be administered to, for example, mammals (such as human, rat, mouse, guinea pig, rabbit, sheep, pig, bovine, horse, cat, dog, monkey, etc.).

Dose levels of the above compound or a salt thereof may vary depending upon the target disease, the patient to be treated, administration route, and so on. When the compound is administered orally for treating Alzheimer's disease, generally the compound is administered to adult patients (60 kg in body weight) at a dose of about 0.1–100 mg/day, preferably about 1.0–50 mg/day, more preferably about 1.0–20 mg/day. With respect to parenteral administration, when the compound is administered to adult patients (60 kg in body weight) in the form of an injection for treating Alzheimer's disease, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, etc. For other animals, corresponding doses may be administered after conversion of the above-mentioned values per 60 kg based on actual body weights.

(8b) Method for Screening for Compounds that Promote or Inhibit Promoter Activity for the DNA of the Invention The present invention provides a method for screening for compounds, or salts thereof, that promote or inhibit promoter activity for the DNA of the invention, which is characterized by administering a test compound to a non-human mammal deficient in expression of the DNA of the invention and detecting the expression of a reporter gene.

In the above screening method, there is used a non-human mammal deficient in expression of the DNA of the invention wherein the DNA of the invention is inactivated as a result of introduction of a reporter gene, and this reporter gene is capable of being expressed under the control of the promoter for the DNA of the invention.

As the test compound, the compounds as enumerated above may be used.

As the reporter gene, the genes as enumerated above may be used. Among all, β-galactosidase gene (lacZ), soluble alkali phosphatase gene or luciferase gene may be preferably used.

In the non-human mammal deficient in expression of the DNA of the invention wherein the DNA of the invention is replaced with a reporter gene, since the reporter gene is present under the control of the promoter for the DNA of the invention, the promoter activity can be detected by tracing the expression of the substance encoded by the reporter gene.

For example, when a part of the DNA region encoding the polypeptide of the invention is replaced with *E. coli*-derived β-galactosidase gene (lacZ), β-galactosidase is expressed instead of the polypeptide of the invention in those tissues where originally the polypeptide of the invention has been expressed. Thus, by staining with a substrate for β-galactosidase such as 5-bromo-4-chloro-3-indolyl-β-D-galactopyrasosidase (X-gal), it is possible to observe the state of in vivo expression of the polypeptide of the invention in the mammal simply. Specifically, nice deficient in the polypeptide of the invention or tissue sections thereof may be fixed in glutaraldehyde or the like, washed with phosphate-buffered physiological saline (PBS), and treated with a staining solution containing X-gal at room temperature or around 37° C. for about 30 min to 1 hr. Subsequently, the tissue samples are washed with 1 mM EDTA/PBS solution to terminate the β-galactosidase reaction, followed by observation of the resultant color development. Alternatively, mRNA encoding lacZ may be detected according to conventional methods.

The compounds or salts thereof obtainable by the above-described screening are compounds that are selected from the above-mentioned test compounds and yet promote or inhibit the promoter activity for the DNA of the invention.

The compound obtained by the above screening may be in a salt form. As salts of the compound, salts formed with physiologically acceptable acids (e.g. organic or inorganic acids) or bases (e.g. alkali metals) may be used. Especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

Since compounds, or salts thereof, that promote the promoter activity for the DNA of the invention can promote the expression of the polypeptide of the invention and thereby promote the function thereof, they are useful as medicines, for example, as prophylactic and/or therapeutic agents for diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases. More preferably, they are useful as prophylactic and/or therapeutic agents for Alzheimer's disease.

Further, those compounds inducible from the compounds obtained from the above screening may also be used in the same manner.

Medicines comprising the compound or, a salt thereof, obtained by the screening may be prepared in the same manner as described for medicines comprising the polypeptide of the invention or a salt thereof.

Since the thus obtained preparations are safe and of low toxicity, they may be administered to, for example, manuals (such as rat, human, mouse, guinea pig, rabbit, sheep, pig, bovine, horse, cat, dog, monkey, etc.).

Dose levels of the above compound or a salt thereof may vary depending upon the target disease, the patient to be treated, administration route, and so on. When a compound that promotes the promoter activity for the DNA of the invention is administered orally for treating Alzheimer's disease, generally the compound is administered to adult patients (60 kg in body weight) at a dose of about 0.1–100 mg/day, preferably about 1.0–50 mg/day, more preferably about 1.0–20 mg/day. With respect to parenteral administration, when a compound that promotes the promoter activity for the DNA of the invention is administered to adult patients (60 kg in body weight) in the form of an injection for treating Alzheimer's disease, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, etc. For other animals, corresponding doses may be administered after conversion of the above-mentioned values per 60 kg based on actual body weights.

On the other hand, when a compound that inhibits the promoter activity for the DNA of the invention is administered orally, generally the compound is administered to adult patients with Alzheimer's disease (60 kg in body weight) at a dose of about 0.1–100 mg/day, preferably about 1.0–50 mg/day, more preferably about 1.0–20 mg/day. With respect to parenteral administration, when a compound that inhibits the promoter activity for the DNA of the invention is administered to adult patients with Alzheimer's disease (60 kg in body weight) in the form of an injection, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, etc. For other animals, corresponding doses may be administered after conversion of the above-mentioned values per 60 kg based on actual body weights.

Thus, the non-human mammal deficient in expression of the DNA of the invention is extremely useful in screening for compounds, or salts thereof, that promote or inhibit the promoter activity for the DNA of the invention, and may contribute greatly to the elucidation of causes of various diseases resulted from deficiency in expression of the DNA of the invention, for example, diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases, or to the development of prophylactic and/or therapeutic agents for such diseases.

In the specification and drawings of the present application, the abbreviations used for bases (nucleotides), amino acids and so forth are those recommended by the IUPAC-IUB Commission on Biochemical Nomenclature or those conventionally used in the art. Examples of such abbreviations are given below. Amino acids that may have optical isomers are intended to represent their L-isomer unless otherwise specified.

DNA: Deoxyribonucleic acid
cDNA: Complementary deoxyribonucleic acid
   A: Adenine
   T: Thymine
   G: Guanine
   C: Cytosine
   RNA: Ribonucleic acid
   mRNA: Messenger ribonucleic acid
   dATP: Deoxyadenosine triphosphate
   dTTP: Deoxythymidine triphosphate
   dGTP: Deoxyguanosine triphosphate
   dCTP: Deoxycytidine triphosphate
   ATP: Adenosine triphosphate
   EDTA: Ethylenediaminetetracetic acid
   SDS: Sodium dodecyl sulfate
   Gly: Glycine
   Ala: Alanine
   Val: Valine
   Leu: Leucine
   Ile: Isoleucine
   Ser: Serine
   Thr: Threonine
   Cys: Cysteine
   Met: Methionine
   Glu: Glutamic acid
   Asp: Aspartic acid
   Lys: Lysine
   Arg: Arginine
   His: Histidine
   Phe: Phenylalanine
   Tyr: Tyrosine
   Trp: Tryptophan
   Pro: Proline
   Asn: Asparagine
   Gln: Glutamine
   pGlu: Pyroglutamic acid The substituents, protective groups and reagents which are frequently used in the specification are represented by the following abbreviations.
   Me: Methyl
   Et: Ethyl
   Bu: Butyl
   Ph: Phenyl
   TC: Thiazolidine-4(R)-carboxamide
   Tos: p-Toluene sulfonyl
   CHO: Formyl
   Bzl: Benzyl
   Cl$_2$-Bzl: 2,6-Dichlorobenzyl
   Bom: Benzyloxymethyl
   Z: Benzyloxycarbonyl
   Cl-Z: 2-Chlorobenzyloxycarbonyl
   Br-Z: 2-Bromobenzyloxycarbonyl
   Boc: t-Butoxycarbonyl
   DNP: Dinitrophenol
   Trt: Trityl
   Bum: t-Butoxymethyl
   Fmoc: N-9-Fluorenylmethyloxycarbonyl
   HOBt: 1-Hydroxybenzotriazole
   HOOBt: 3,4-Dihydro-3-hydroxy-4-oxo-1,2,3-benzotriazine
   HONB: 1-Hydroxy-5-norbornene-2,3-dicarboximide
   DCC: N,N'-Dicyclohexylcarbodiimide
   Pbf: 2,2,4,6,7-Pentanethyldihydrobenzofuran-5-sulfonyl
   tBu: Tertiary butyl
   TFA: Trifluoroacetate
   OHAt: 1-Hydroxy-7-azabenzotriazol
   PyAop: 7-Azabenzotriazole-1-yloxytris(pyrrolidino) phosphonium hexafluorophosphate
   DIPCDI: 1,3-Diisopropyl-carbodiimide
   Fmoc-Leu-Ser(Psi(Me,Me)pro)-OH: (4S)-3-(Fmoc-Leu)-2,2,-dimethyloxazolidine-4-carboxylic acid)]

The SEQ ID NOS of the SEQUENCE LISTING of the present specification represent the sequences as indicated below.

[SEQ ID NO: 1]
This shows the nucleotide sequence of a primer used in Example 1.
[SEQ ID NO: 2]
This shows the nucleotide sequence of a primer used in Example 1.
[SEQ ID NO: 3]
This shows the nucleotide sequence of a DNA encoding the polypeptide of the invention obtained in Example 1.
[SEQ ID NO: 4]
This shows the amino acid sequence of the polypeptide of the invention obtained in Example 1.
[SEQ ID NO: 5]
This shows the nucleotide sequence of a query used in Example 1.
[SEQ ID NO: 6]
This shows the nucleotide sequence of the DNA obtained in Example 1 comprising the SEQ ID NO: 3.
[SEQ ID NO: 7]
This shows the amino acid sequence of a partial peptide of the polypeptide of the invention (SEQ ID NO: 4) obtained in Example 1.
[SEQ ID NO: 8]
This shows the nucleotide sequence of a DNA encoding SEQ ID NO: 7.

Transformant *Escherichia coli* TOP10/pcDNA-hn3 obtained in Example 1 described later has been deposited with the International Patent Organism Depository, National Institute of Advanced Industrial Science and Technology located at Central 6, 1-1 Higashi 1-chome, Tsukuba City, Ibaraki Pref. (zip code No.: 305-8566) since Jul. 19, 2001 wider the Accession No. FERM BP-7674 and with the Institute for Fermentation, Osaka (IFO) located at 17–85, jusanbonncho 2-chome, Yodogawa-ku, Osaka City, Osaka Pref. (zip code No.:532–8686) since Jul. 3, 2001 under the Accession No. IFO 16673.

EXAMPLES

Hereinbelow, the present invention will be described more specifically with reference to the following Examples. However, the present invention is not limited to these Examples. Genetic manipulations using *E. coli* were carried out in accordance with the methods described in the book "Molecular Cloning".

Example 1

Database GEMBLE was searched for using the human humanin-like gene coding region as a query. As a result, it was found that a humanin-like gene region comprising a start codon and a termination codon both corresponding to the coding region of the humanin gene is present within the sequence of Accession No. AL356135. In order to confirm that this gene exists actually and that this gene is transcribed and functions, the inventors have prepared a cDNA by reverse transcription using 1.0 µg of human total brain poly A$^+$ RNA (Clontech) as a template, SuperScript reverse transcriptase (Gibco BRL) and, according to the manual attached to the transcriptase, Oligo (dT) primers. Then, two primers TACCCTAACCGTGCAAAGGTAGCATG (SEQ ID NO: 1) and GTGGGCTTATTGGGTGTTGTTTGCAT-TGG (SEQ ID NO: 2) located upstream of 5' end and downstream of 3' end, respectively, of the humanin-like sequence in Accession No. AL356135 sequence were designed, followed by a PCR in 20 µl of a reaction solution. This reaction solution was composed of the cDNA solution as a template in an amount equivalent to 10 ng of mRNA, 0.5 µM each of the primers, 2.5 mM MgCl$_2$, 0.2 mM dNTP, 1/100 volume of AmpliTaq Gold (Perkin Elmer), and 1/10 vlume of 10× AmpliTaq Gold Buffer. Following the first denaturation at 95° C. for 10 min, 40 cycles of at 95° C. for 15 sec, at 67° C. for 15 sec and at 72° C. for 15 sec were performed, followed by final extension at 72° C. for 5 min. The amplified DNA in the resultant solution was sub-cloned into plasmid vector pcDNA3.1/V5/His-TOPO using Eukaryotic TOPO TA cloning kit (Invitrogen) and then introduced into *E. coli* TOP10. From the resultant transformant, plasmid DNA was purified using QIA prep8 mini prep (Qiagen). Reactions for determining the nucleotide sequence were performed using BigDye Terminator Cycle Sequence Ready Reaction Kit (Perkin Elmer) and analyzed with an automated fluorescence sequencer. As a result, a nucleotide sequence as shown in SEQ ID NO: 6 was obtained which comprises the coding region of the humanin-like sequence (SEQ ID NO: 3) found in the above-described search. Thus, it was confirmed that this gene is expressed in human total brain.

Since this sequence (SEQ ID NO: 6) comprises the full length of the coding region of the humanin-like sequence, *E. coli* TOP10 was transformed with the above-described plasmid to thereby obtain of *Escherichia coli* TOP 10/pcDNA-hn3.

Example 2

A polypeptide comprising the amino acid sequence as shown in SEQ ID NO: 4 is sometimes referred to as a "humanin-like peptide".

A humanin-like peptide was prepared as described below.

Briefly, 0.25 mmol of Fmoc-Thr(tBu)-O-Clt resin (0.527 mmol/g) [wherein Fmoc-Thr(tBu)-OH is introduced into a commercial 2-chlorotrityl resin (Clt resin, 1.33 mmol/g)] was placed in the reactor of a peptide synthesizer ABI 433A, and solid-phase peptide synthesis was performed by the Fmoc/DCC/HOBt method. As the side-chain protective groups for Fmoc amino acids, Pbf group was used for Arg; Boc group was used for Lys; tBu group was used for Asp, Thr and Ser; and Trt group was used for Cys. Other amino acids were used without side-chain protective groups. The peptide chain was extended to position 13 of the above-mentioned sequence (Thr). To the resultant Fmoc-humanin-like peptide (13-24)-0-Clt resin, Fmoc-Leu-Ser(Psi(Me,Me)pro)-OH (NOVA; product No. 05-20-1004) was introduced with DIPCDI/HOAt. Then, amino acids were introduced in order from Leu at position 10 toward the N-terminal with DCC/HOBt, to thereby obtain a protected peptide resin of interest.

This resin (100 mg) was agitated in a mixed solution (total 1.5 ml) of TFA, thioanisole, m-cresol, water, triisopropyl-silane and ethanidithiol (80:5:5:5:2.5:2.5) at room temperature for 1.5 hrs. Then, ether was added to the reaction solution to deposit white powder. The reaction solution was centrifuged, followed by removal of the supernatant. These operations were repeated three times. The resultant residue was extracted with water and then lyophilized to obtain white powder. The thus obtained crude peptide was subjected to preparative HPLC using YMC Pack R&D-ODS-5-B S-5, 120A column (30× 250 nm). A linear-type concentration gradient elution (60 min) was performed using mobile phase A (0.1% TFA in water) and mobile phase B (0.1% TFA in acetonitrile) at A/B ratios of from 78/22 to 68/32. Fractions containing the peptide of interest were collected and lyophilized to obtain 21.8 mg of white powder.

ESI-MS: M$^+$ 2692.8 (theoretical value: 2692.5)
HPLC elution time: 10.5 min
Elution conditions:
Column YMC AM 301 (4.6×100 mm)
Mobile phase A: 0.1% TFA in water; B: 0.1% TFA in acetonitrile
A/B: from 80/20 to 30/70, linear-type concentration gradient elution (25 min)
Flow rate: 1.0 ml/min Example 3

Inhibitory Activity of the Humanin-Like Peptide against Glutanic Acid-Induced Cell Death of Rat Adrenal Medulla-Derived Pheochromocytoma Cell PC12h PC12h cells (supplied by Prof. Hiroshi Hatanaka, Institute for Protein Research, Osaka University; Hatanaka, H., Brain Research 222: 225–233, 1981) were plated at a density of 2×10$^4$ cells/cm$^2$ in collagen-coated 96-well plates (Iwaki) containing Dulbecco's modified Eagle's medium (hereinafter referred to as "DMEM") containing 10% fetal bovine serum and 5% horse serum. After 24 hrs, the medium was exchanged for 100 µl of DMEM containing 20 nM HEPES (pH 7.5). At the same time, various concentrations of the humanin-like peptide prepared in Example 2 (SEQ ID NO: 4) and glutamic acid to give a concentration of 1 mM were added to the medium. After 72 hrs, cells were lysed with 100 µl of phosphate buffered saline containing 0.2% Tween 20. Then, the lactate dehydrogenase (LDH) activity of the cell extract was determined with LDH Cytotoxic Test WAKO (Wako Purechemical Industries).

The results are shown in FIG. 1.

Seventy-two hours after the glutamic acid treatment, while cell survival ratio was 34.0% in the humanin-like peptide not-added plot, the survival ratios were improved to 59.3% and 74.6%, respectively, by the addition of the humanin-like peptide at-1 µM and 10 µM. Here, cell survival ratios are expressed taking the survival in the glutamic acid non-added plot as 100%.

From these results, it is clear that glutamic acid-induced cell death of rat adrenal medulla-derived pheochromocytoma cell PC12h is inhibited by the humanin-like peptide.

Example 4

Preparation of Another Humanin-Like Peptide (19–24) (SEQ ID NO: 7): Pro-Val-Lys-Arg-Arg-Thr A protected peptide resin having the sequence of interest was prepared using Fmoc-Thr(tBu)-O-Clt resin, and purified in the same manner as described for the humanin-like peptide prepared in Example 3. As a result, 29 mg of white powder was obtained.

ESI-MS: M$^+$ 756.5 (theoretical value: 756.5)
HPLC elution time: 10.2 min
Elution conditions:
Column YMC AM 301 (4.6×100 mm)
Mobile phase A: 0.1% TFA in water; B: 0.1% TFA in acetonitrile
A/B: from 80/20 to 30/70, linear-type concentration gradient elution (25 min)
Flow rate: 1.0 ml/min

INDUSTRIAL APPLICABILITY

The polypeptide and the polynucleotide of the invention can be used as a diagnostic, therapeutic and/or prophylactic agent for various diseases including diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotrophic lateral sclerosis, prion disease, Creutzfeldt-Jacob disease, Huntington's chorea, diabetic neuropathy, multiple sclerosis, etc.], brain dysfunctions (e.g. brain infarction, cerebral hemorrhage, subarachloid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases; or as a cell death inhibitor. The polypeptide of the invention is also useful as a reagent for screening for those compounds or salts thereof which promote or inhibit the activity of the polypeptide of the invention. Further, since antibodies to the polypeptide of the invention can recognize the polypeptide of the invention specifically, they can be used in the detection, quantitative determination or neutralization of the polypeptide of the invention in sample solutions, and are useful in the diagnosis of various diseases including diseases accompanied by neurodegeneration, such as neurodegenerative diseases [e.g. Alzheimer's disease (familial Alzheimer's disease, juvenile Alzheimer's disease, sporadic Alzheimer's disease, etc.), Parkinson's disease, Down syndrome, amyotroplic lateral sclerosis, prion disease, Creutzfeldt-Jacob disease. Huntington's chorea, diabetic neuropathy, multiple sclerosis, etc.], brain dysfunctions (e.g. brain infarction, cerebral hemorrhage, subarachnoid hemorrhage, ischemic brain diseases, epidural hematoma, subdural hematoma, etc.), cancers (e.g. astrocytoma, oligodendroglioma, etc.), immunological diseases, infections (e.g. meningitis, protozoiasis, rickettsial infections, metazoan infections, bacterial or viral meningitis such as Borna's disease, postvaccinal encephalitis, AIDS encephalopathy, etc.), gastrointestinal diseases, circulatory diseases and endocrine diseases.

---

The invention claimed is:

1. A polypeptide comprising an amino acid sequence as shown in SEQ ID NO: 4, or an amide, ester or salt thereof.

2. The polypeptide according to claim 1 consisting of the amino acid sequence as shown in SEQ ID NO: 4, or an amide, ester or salt thereof.

3. A method for producing the polypeptide according to claim 1 or an amide, ester or salt thereof, comprising
culturing a transformant transformed with a recombinant vector comprising a polynucleotide having a nucleotide sequence encoding the polypeptide according to claim 1; and
allowing the polypeptide according to claim 1 to be produced and accumulated.

4. A method for screening for compounds, or salts thereof, that promote or inhibit the activity of the polypeptide according to claim 1 or an amide, ester or salt thereof, wherein the method is characterized by using the polypeptide according to claim 1 or an amide, ester or salt thereof.

5. A kit for screening for compounds, or salts thereof, that promote or inhibit the activity of the polypeptide according to claim 1 or an amide, ester or salt thereof, which comprises the polypeptide according to claim 1 or an amide, ester or salt thereof.

6. A medicine comprising the polypeptide according to claim 1 or an amide, ester or salt thereof.

7. The medicine according to claim 6, wherein said medicine is a prophylactic and/or therapeutic agent for neurodegenerative disorders or brain dysfunctions.

8. The medicine according to claim 7, wherein said medicine is a prophylactic and/or therapeutic agent for Alzheimer's disease, Parkinson's disease, Down syndrome, amyotrophic lateral sclerosis, prion disease, Creutzfeldt-Jacob disease, Huntington's chorea, diabetic neuropathy, multiple sclerosis, brain infarction, cerebral hemorrhage, subarachnoid hemorrhage, ischemic brain diseases, epidural hematoma or subdural hematoma.

9. The medicine according to claim 7, wherein said medicine is a prophylactic and/or therapeutic agent for Alzheimer's disease.

10. The medicine according to claim 6, wherein said medicine is a cell death inhibitor.

11. A method of preventing and/or treating neurodegenerative diseases or brain dysfunctions, which is characterized by administering to a mammal an effective amount of the polypeptide according to claim 1 or an amide, ester or salt thereof.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
taccctaacc gtgcaaaggt agcatg      26

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
gtgggcttat tgggtgttgt ttgcattgg      29

<210> SEQ ID NO 3
<211> LENGTH: 72
<212> TYPE: DNA
<213> ORGANISM: Human

<400> SEQUENCE: 3
atggctcgac gaggtttcag ctgtctctta ctttcaacca ctgcaactga cctgcccgtg      60

```
aagaggcgga ca                                                     72

<210> SEQ ID NO 4
<211> LENGTH: 24
<212> TYPE: PRT
<213> ORGANISM: Human

<400> SEQUENCE: 4

Met Ala Arg Arg Gly Phe Ser Cys Leu Leu Leu Ser Thr Thr Ala Thr
 1               5                  10                  15

Asp Leu Pro Val Lys Arg Arg Thr
            20

<210> SEQ ID NO 5
<211> LENGTH: 75
<212> TYPE: DNA
<213> ORGANISM: Human

<400> SEQUENCE: 5
atggctccac gagggttcag ctgtctctta cttttaacca gtgaaattga cctgcccgtg   60
aagaggcggg cataa                                                   75

<210> SEQ ID NO 6
<211> LENGTH: 145
<212> TYPE: DNA
<213> ORGANISM: Human

<400> SEQUENCE: 6
atcacttgtt ccttaaatag ggacttgtat gaatggctcg acgaggtttc agctgtctct   60
tactttcaac cactgcaact gacctgcccg tgaagaggcg gacataatac aacaagacga  120
gaagaccata tggagcttca attta                                       145

<210> SEQ ID NO 7
<211> LENGTH: 6
<212> TYPE: PRT
<213> ORGANISM: Human

<400> SEQUENCE: 7

Pro Val Lys Arg Arg Thr
 1               5

<210> SEQ ID NO 8
<211> LENGTH: 18
<212> TYPE: DNA
<213> ORGANISM: Human

<400> SEQUENCE: 8
cccgtgaaga ggcgggca                                                18
```